(12) United States Patent
Steiger et al.

(10) Patent No.: US 6,235,914 B1
(45) Date of Patent: May 22, 2001

(54) AMINE AND QUATERNARY AMMONIUM COMPOUNDS MADE FROM KETONES AND ALDEHYDES, AND COMPOSITIONS CONTAINING THEM

(75) Inventors: Philip Howard Steiger, Powell; Christopher Joseph Toney, Columbus, both of OH (US)

(73) Assignee: Goldschmidt Chemical Company, Hopewell, VA (US)

( * ) Notice: Subject to any disclaimer, the term of this patent is extended or adjusted under 35 U.S.C. 154(b) by 0 days.

(21) Appl. No.: 09/642,521

(22) Filed: Aug. 18, 2000

Related U.S. Application Data

(60) Provisional application No. 60/150,518, filed on Aug. 24, 1999.

(51) Int. Cl.$^7$ .................................. C07B 43/00
(52) U.S. Cl. ..................... 554/114; 554/103; 554/110; 564/281; 564/291; 564/292; 564/296; 252/8.61; 252/8.81
(58) Field of Search ................... 554/103, 106, 554/110, 114; 564/281, 291, 292, 296; 252/8.61, 8.81

(56) References Cited

U.S. PATENT DOCUMENTS 5,580,575  12/1996  Unger et al. .

*Primary Examiner*—Deborah D. Carr
(74) *Attorney, Agent, or Firm*—Scully, Scott, Murphy & Presser

(57) ABSTRACT

A process for making a tertiary amine ester of the following formula (I):

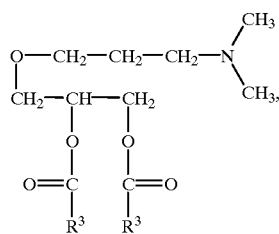

the process comprising:

(a) reacting a ketone or an aldehyde having the formula

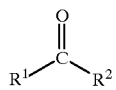

with a glycol to form a ketal or an acetal;

(b) reacting the ketal or the acetal with acrylonitrile to form an ether nitrile;

(c) reducing the ether nitrile to a tertiary amine ketal or a tertiary amine acetal;

(d) hydrolyzing the tertiary amine ketal or the tertiary amine acetal to a tertiary amine diol; and (e) esterifying the tertiary amine diol to the tertiary amine ester of formula (I), wherein $R^1$ and $R^2$ are each independently a hydrogen atom or a linear, branched, or cyclic alkyl, alkylene, alkaryl, or aryl-containing group containing 1 to 18 carbon atoms; and each $R^3$ are each independently of one another fatty acid radicals having 6–22 carbon atoms. The process may optionally include the further step of:

(f) protonating or quaternizing the tertiary amine ester of formula (I) to a protonated or quaternary amine ester of the following formula:

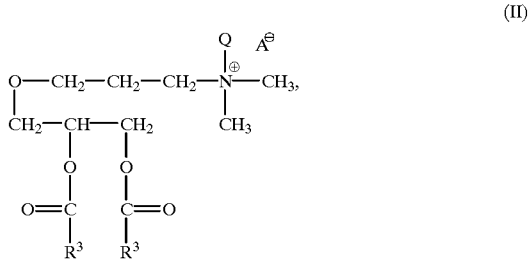

wherein $A^-$ is an inorganic or organic anion.

33 Claims, No Drawings

AMINE AND QUATERNARY AMMONIUM COMPOUNDS MADE FROM KETONES AND ALDEHYDES, AND COMPOSITIONS CONTAINING THEM

RELATED APPLICATIONS

This application claims benefit of U.S. Provisional Application Ser. No. 60/150,518 filed Aug. 24, 1999.

BACKGROUND OF THE INVENTION

The present invention relates to quaternary ammonium compounds and formulations thereof useful as, for instance, cleaning compositions, antistatic compounds, fabric softeners, hair conditioners, skin conditioners, paper deinking and ink floatation agents, asphalt emulsion agents, corrosion inhibitor agents, ore floatation agents, pesticide emulsion agents, car drying aid sprays, drilling fluid additives, and the like.

Heretofore quaternary ammonium compounds and a very few dialkyl ammonium compounds ("conventional quats") have found widespread use in many applications. For example, a variety of conventional quats have been proposed for many uses, for example, in fabric softeners for home use or for industrial and institutional use. In general, such compounds exhibit properties which present some difficulty in the manufacture, formulation use, aesthetic properties, biodegradability, and environmental compatibility of these compositions. For example, many of the conventional compositions used for these functions, even if completely biodegradable with time, do not biodegrade as rapidly as could be desired and are thus not considered readily biodegradable. In addition, several of the commercial readily biodegradable softeners, conditioners, and debonders do not function as effectively as the conventional products that are less biodegradable. Thus, to maintain effective levels of performance, increased amounts of such less effective, more readily biodegradable products (such as softeners) must be employed and, as will be readily apparent, this factor decreases the cost-effectiveness of the product.

The relatively poor solubility of conventional quats also contributes to certain difficulties that will vary, depending on the application. For example, when such conventional quats are used in fabric softeners, their poor solubility inhibits the dispersibility of the fabric softener actives into water and the dispersibility of the formulated fabric softener product into the washing machine. In washing of textiles, the rinse softeners are often used in the last washing stage. In this way, coarsening of the fabric is lessened which otherwise could be realized upon drying. The feel of textiles treated in this way such as hand and bath towels as well as clothes and bed linens is pleasantly improved.

Cationic compounds are customarily used as rinse softeners, for example, quaternary ammonium compounds which can contain long-chain alkyl groups as well as ester groups or amide groups, such as are described in U.S. Pat. Nos. 3,349,043; 3,644,203; 3,946,115; 3,997,453; 4,073, 735; and 4,119,545. These quaternary ammonium compounds are added to the rinse water by themselves or in mixtures with other cationic or neutral compounds in the form of aqueous dispersions.

In addition, quaternary ammonium compounds which contain ester linkages are frequently used, such as are described in EP-A-023910, U.S. Pat. Nos. 3,915,867; 4,137, 180; and 4,830,771. Particularly widely used are ester compounds based on triethanolamine such as N-methyl, N,N-bis($\beta$-$C_{14\text{-}18}$-acyloxyethyl), N-$\beta$-hydroxyethyl ammonium methylsulfate, which are available from Kao Corporation under tradename TETRANYL® AT 75, from Stepan Corporation under the tradename STEPANTEX® ZRH 90, and from Witco Surfactants GmbH under the tradename REWOQUAT® WE 18. While these cationic compounds exhibit effective softening when used in the last rinse stage, they exhibit some disadvantages during use. For example, one disadvantage is that a relatively large amount of softening agents is required to simultaneously obtain good rewettability and soft feel of textiles, although the softness is still unsatisfactory. Rewetting power or rewettability is generally taken to mean the absorption of moisture by the fiber. Inadequate rewetting power is, however, disadvantageous wherever relatively large amounts of moisture are to be absorbed from the surface of the skin, for example, in the case of hand or bath towels and in the case of underwear or bed linen. However, batch or continuous processes are known that can be used to prepare stable fabric softener dispersions using these products.

Thus, there remains a need for identification of new amine and ammonium derivatives, and particular quaternary derivatives, which are useful as fabric softeners and which are also biodegradable, highly effective in softening, debonding, conditioning, and the like, and yet avoid these problems upon manufacture, formulation and use. It is also desirable for the active agents used in hair and skin conditioners, textile softeners, and the like, to be readily biodegradable and to exhibit a satisfactorily high activity. Conventional products have to date not been able to exhibit both properties to a high degree, thus necessitating acceptance of reduced biodegradability or reduced activity. There is thus still a need for compounds exhibiting levels of activity as conditioners, and so on, as the case may be, which are comparable or superior to conventionally employed actives, such as conventional quats, while also exhibiting ready biodegradability.

As can be appreciated, the chemistry of fabric softeners, hair conditioners, skin conditioners, textile softeners, car wax sprays, and the like is challenging. Each of these applications presents its own complications, because the interactions between the various components of the compositions must be considered in addition to the individual chemistry of each component. For example, considering the fabric softening application, the detergent compounds with the widest range of cleaning properties are generally anionic (negatively charged) surfactants. Such anionic surfactants, for example, may include the alkylbenzene sulfonates, α-olefin sulfonates, and xylene sulfonates available from Witco Corporation under the WITCONATE® trademark. In contrast, as exemplified by the amine and ammonium compounds discussed above, fabric softening compounds are generally cationic (positively charged). Thus, when the anionic detergent ingredients and cationic softening ingredients are present in the same aqueous solution, they have a natural tendency to complex together or even precipitate out of solution. This complexation or precipitation reaction interferes with the performance of both the detergent compounds and the softening compounds and is therefore undesirable. It can be readily appreciated that this undesirable complexation or precipitation reaction may occur if both detergent and softener compounds are added together in a wash cycle; however, as North American washing machines typically rinse the clothes only once before fabric softener is added to the washload, even if the fabric softener is added during a rinse cycle (as is typically done), residual anionic detergent compounds (including builders) present in the fabric complexes with the cationic softener compounds.

SUMMARY OF THE INVENTION

The present invention achieves these objectives and also exhibits the properties and advantages described herein. The present invention relates to a process for making certain novel ester amine compounds and the salts and quaternary ammonium compounds thereof, and the compounds made by the instant process. The present invention also relates to the compounds made by the instant process and formulations thereof useful as, for instance, cleaning compositions, antistatic compounds, fabric softeners, hair conditioners, skin conditioners, paper deinking and ink floatation agents, asphalt emulsion agents, corrosion inhibitor agents, ore floatation agents, pesticide emulsion agents, car drying aid sprays, drilling fluid additives, and the like.

An object of the present invention was to overcome the abovementioned disadvantages of traditional fabric softener formulations and to provide laundry fabric softeners which, in addition to good biodegradability, have a significantly improved level of simultaneously good soft handle and rewetting power.

One aspect of the instant invention provides a process for making a tertiary amine ester of the following formula (I):

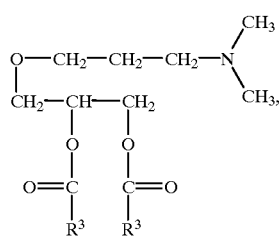
(I)

the process comprising:
(a) reacting a ketone or an aldehyde having the formula

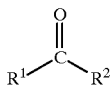

with a glycol to form a ketal or an acetal;
(b) reacting the ketal or the acetal with acrylonitrile to form an ether nitrile;
(c) reducing the ether nitrile to a tertiary amine ketal or a tertiary amine acetal;
(d) hydrolyzing the tertiary amine ketal or the tertiary amine acetal to a tertiary amine diol; and
(e) esterifying the tertiary amine diol to a tertiary amine ester,
wherein $R^1$ and $R^2$ are each independently a hydrogen atom or a linear, branched, or cyclic alkyl, alkylene, alkaryl, or aryl-containing group containing 1 to 18 carbon atoms, and
each $R^3$ are each independently of one another fatty acid radicals having 6–22 carbon atoms.

Another aspect of the instant invention provides a process for making a protonated or quaternary amine ester of the following formula:

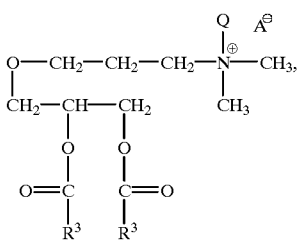
(II)

the process comprising:
(a) reacting a ketone or an aldehyde having the formula

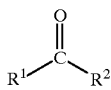

with a glycol to form a ketal or an acetal;
(b) reacting the ketal or the acetal with acrylonitrile to form an ether nitrile;
(c) reducing the ether nitrile to a tertiary amine ketal or tertiary amine acetal;
(d) hydrolyzing the tertiary amine ketal or tertiary amine acetal to a tertiary amine diol;
(e) esterifying the tertiary amine diol to a tertiary amine ester; and
(f) protonating or quaternizing the tertiary amine ester to the protonated or quaternary amine ester,
wherein $R^1$ and $R^2$ are each independently a hydrogen atom or a linear, branched, or cyclic alkyl, alkylene, alkaryl, or aryl-containing group containing 1 to 18 carbon atoms
each $R^3$ are each independently of one another fatty acid radicals having 6–22 carbon atoms;
Q is —H, $CH_3$ or —$C_2H_5$; and
$A^-$ is an inorganic or organic anion. In general, $A^-$, whether shown or understood, may be selected, without limitation, from the group consisting of fluoride, chloride, bromide, iodide, chlorite, chlorate, hydroxide, hypophosphite, phosphite, phosphate, carbonate, formate, acetate, lactate, and other carboxylates, oxalate, methyl sulfate, ethyl sulfate, benzoate, and salicylate, and the like. Preferred examples of the anions are chloride, bromide, methyl sulfate, ethyl sulfate, and salicylate.

In preferred embodiments of the invention, the composition includes water in the formulation. In other preferred embodiments of the invention, the composition comprises a mixture of two or more different compounds of formulas (I) and/or (II). The invention also provides compositions comprising compounds of the general formula (I) and/or (II); in preferred embodiments of such compositions the amount of compounds of the general formula (I) and/or (II) generally ranges from about 2 wt. % to about 80 wt. %, preferably 5 wt. % to 30 wt. %, and more preferably 6 wt. % to 25 wt. %, of the total composition. The invention additionally provides compositions comprising compounds of the general formula (I) and/or (II) in combination with conventional quaternary ammonium compounds that comprise from about 10% to about 90% by weight of the total amount of quaternary ammonium compounds, which is the compounds of the general formula (I) and/or (II) and the conventional quaternary ammonium compounds, in the composition. Other preferred embodiment of the instant invention comprises compounds of the general formula (I) and/or (II) in combination with water.

The invention further provides compositions comprising at least one of the compounds of the general formula (I) and/or (II), useful for many applications, for example, as fabric softeners. In the fabric softener application, the composition is contemplated to be applied in any of the many conventional ways fabric softeners are applied to fabrics. For example, the compositions of the instant invention may be applied or used at any time in the wash cycle of a washing machine, for example, in a prewash cycle, wash cycle, or postwash (rinse) cycle by adding such composition to the wash or rinse water or spraying directly on the clothes. In addition, the compositions of the instant invention may be applied or used at any time previous or subsequent to the fabric being placed in a washing machine, for example, in a clothes dryer by use of a fabric softener dryer sheet impregnated with one of the compounds of the general formula (I) and/or (II), or by spraying a formulation comprising one of the compounds of the general formula (I) and/or (II) on the fabric at any time before or after washing.

The invention also provides compositions comprising compounds of the general formula (I) and/or (II), which may optionally include from about 1% to about 20% by weight of a secondary surfactant selected from the group consisting of: nonionic surfactants, amphoteric surfactants, zwitterionic surfactants, and ionic surfactants. In preferred embodiments, the secondary surfactant is selected from the group consisting of: ammonium lauryl sulfate, sodium lauryl sulfate, any α-olefin sulfonate, ammonium laureth sulfate (2 or 3 moles), sodium laureth sulfate (2 or 3 moles), sodium myristyl sulfate, sodium myristeth sulfate (1–4 moles), ammonium xylene sulfonate, sodium xylene sulfonate, TEA dodecylbenzene sulfonate, TEA lauryl sulfate, ammonium pareth sulfate, sodium pareth sulfate, sodium oleth sulfate, derivatives thereof, and mixtures thereof. In other preferred embodiments, the secondary surfactant is selected from the group consisting of: betaines, sulfosuccinates, mono- and diglycerides, glycinates, sugars and derivatives thereof, hydroxysultaines, mono- and diacetates, ethoxylated derivatives thereof, and mixtures thereof. In yet other preferred embodiments, the secondary surfactant is selected from the group consisting of: alkanolamides; amine oxides; nonylphenol ethoxylates; $C_5$–$C_{20}$ linear or branched alcoxylates using EO, PO, BO, or mixtures thereof; amine ethoxylates; fatty amide ethoxylates; fatty acid ethoxylates; carboxylated nonionics; α-polyglucosides; and mixtures thereof. In still other preferred embodiments, the formulation further comprises water and/or about 0.1% to 10% by weight of thickeners, perfumes, preservatives, dyes, plant extracts and other additives and auxiliaries.

The invention further provides for the use of compounds of the general formulas (I) and/or (II) in amounts of 1–5% by weight for the preparation of hair or skin conditioner compositions with use of auxiliaries and additives customary in this field. Hair or skin conditioner compositions are taken to mean applications such as hair treatments, hair rinses, hair balsam, hair mousses, spray lotions for improving combability, conditioning shampoos, shower gels, and liquid soaps having a smoothing effect on the skin.

The invention further provides for the use of 5–20% by weight of the compounds of the general formula (I) and/or (II) for the preparation of detergents and rinses and drying auxiliaries for motor vehicles with use of the additives and auxiliaries customary in this field, such as solvents, viscosity regulators, fatty acid esters, and additional surfactants.

The compounds of the general formulas (I) and/or (II) can, in combination with other surfactants and/or silicone compounds, be used as hydrophilic handle modifiers for yarns, fabrics and other textiles made from synthetic and mixed fibers and, preferably, from natural fibers, in which case they impart excellent antistatic properties, good handle, and hydrophilicity to the textiles without causing yellowing. The handle modifiers are used as 1–10% strength dispersions, coverage being 1–15%. The invention thus further provides for the use of the compounds of the general formulas (I) and/or (II) for the preparation of hydrophilic handle modifiers for yarns, fabrics and other textiles, comprising 15% to 25% by weight of alkyl fatty acid polyglycol ester having 6 to 25 moles of EO, 45% to 65% by weight of compounds of the general formula (I) and/or (II), 10–20% by weight of partial glyceride esters having 5 to 80 moles of EO, and 5% to 10% by weight of alkyl ether citrates (monoesters, diesters, and triesters having a degree of ethoxylation of 5 to 15), with the proviso that the components total 100% by weight. In preferred embodiment, the hydrophilic handle modifier compositions further comprise 0.001% to 10% by weight of silicone compounds; most preferably from about 0.01% to about 5% by weight of silicone compounds. In another preferred embodiment of the invention, the silicone compounds comprise silicone compounds of the polydimethylsiloxane and cationically-modified polydimethylsiloxane type.

The compounds of the general formula (I) and/or (II) can be used as such or in combination with other surfactants and/or silicone compounds as preparations for the permanent hydrophilization of polyolefin or polyester fibers and filaments and the nonwovens prepared therefrom. The permanent hydrophilization compositions are used as 1% to 10% strength dispersions, coverage being 1% to 15%. The surface-active constituents which are also used are preferably based on vegetable raw materials. The invention thus further provides for the use of the compounds of the general formula (I) and/or (II) for the preparation of permanent hydrophilization compositions comprising: 15% to 30% by weight of alkyl fatty acid polyglycol esters having 6 to 25 moles of EO; 45% to 65% by weight of compounds of the general formula (I) and/or (II); and 5% to 10% by weight of alkyl ether citrates (monoesters, diesters, and triesters having a degree of ethoxylation of 5 to 15), with the proviso that the components total 100% by weight. In preferred embodiment, the permanent hydrophilization compositions further comprise 0.001% to 10% by weight of silicone compounds, most preferably from about 0.01% to about 5% by weight of silicone compounds. In another preferred embodiment, the silicone compounds comprise silicone compounds of the polydimethylsiloxane and cationically-modified polydimethylsiloxane type.

The invention also provides a detergent, rinse, or drying auxiliary formulation for cars, comprising: (a) from about 5% to about 20% by weight of at least one quaternary ammonium compound selected from the group consisting of compounds of the general formula (I) and the general formula (II); and (b) from about 1% to about 20% by weight of a secondary surfactant selected from the group consisting of: nonionic surfactants, amphoteric surfactants, zwitterionic surfactants, and ionic surfactants, and blends thereof. In preferred embodiments, the secondary surfactant is selected from the group consisting of: alkylbenzene stilfonates, α-olefin sulfonates, and xylene sulfonates.

The present invention also provides a composition comprising: (a) at least one compound selected from the group consisting of compounds of the general formula (I) and the general formula (II); (b) a solvatrope or coupling agent or blends thereof; and (c) an oil or hydrophobic organic component and blends thereof. In a preferred embodiment of the invention, the composition further comprises water. In yet another preferred embodiment of the invention, the amount of the compound of formula (I) and/or (II) is about 0.1 wt. % to about 65 wt. % of the formulation; the amount of solvatrope or coupling agent is about 0.1 wt. % to about 65 wt. % of the formulation, the amount of oil or hydrophobic organic component is about 0.1 wt. % to 65 wt. % of the formulation, and the amount of water is about 20 to 99.7 wt. % of the formulation, preferably about 35 wt. % to about 99.7 wt. %. In still other preferred embodiments of the invention, the composition comprises a mixture of two or more different solvents or coupling agents or the solvatrope or coupling agent is selected from the group consisting of: hydroxypivalyl hydroxypivalate and its alkoxylated derivatives, TMPD, TMPD alkoxylates, ethanol, isopropanol, butanol, 1,2-cyclohexanedimetlianol, 1,4-cyclohexanedimetilanol, HPHP glycol, isopentyidiol, 1,2-hexanediol, ethylene glycol butyl ether, hexylene glycol, isoprene glycol, sorbitan ethoxylates, 2-butoxyethanol, $C_6$–$C_{12}$ diols/triols and ester diols/triols and their alkoxylated derivatives, glycol ethers, and mixtures thereof. In another preferred embodiment of the invention, the oil or hydrophobic organic component is selected from the group consisting of: fatty acids; fatty amides; fatty alcohols; fatty oils; fatty esters made from a $C_8$–$C_{22}$ fatty acid and a $C_1$–$C_8$ alcohol; dialkyl esters; mineral oil; mineral seal oils; silicone oils; petrolatums; monoglycerides; diglycerides; triglycerides; aliphatic, paraffinic, and naphthalinic hydrocarbons; oils and spirits; and mixtures thereof. In yet another preferred embodiment of the invention, the composition comprises a personal care emollient, which may be selected from the group consisting of: acetylated lanolin, aminopropyl dimethicone, ammonium hydrolyzed collagen, ammonium lauroyl sarcosinate, amodimethicone, amodimethicone/dimethicone copolyol, amodimethicone hydroxystearate, capryloyl hydrolyzed collagen, cetyl alcohol, cetyl esters, cetyl laurate, cocamidopropyl dimethylamine dihydroxymethylpropionate, cocoyl hydrolyzed soy protein, collagen, disodium cocoamphodiacetate, disodium cocoamphodipropionate, dioctyl dimerate, ditridecyl adipate, glycerine, glyceryl oleate, glyceryl stearate, hydrogenated soybean oil, hydrogenated tallow glycerides, isocetyl stearate, jojoba (*Buxus chinensis*) oil, keratin, lanolin, milk protein, mineral oil, oat (*Avena sativa*) protein, octyl cocoate, oleyl myristate, oleyl stearate, palm alcohol, palm glycerides, panthenol, PEG-10, PEG-32, PEG-100, PEG-200, petrolatum, PPG-6-sorbeth-245, stearyl citrate, tridecyl stearate, urea, vegetable oil, wheat amino acids, and mixtures thereof. In another preferred embodiment of the invention, the composition further comprises a personal care emulsifier, which may be selected from the group consisting of: beheneth-5, beheneth-10, beheneth-20, butylglucoside caprate, ceteareth-2, ceteareth-1, ceteareth-18, ceteth-10, ceteth-16, corn oil PEG-8 esters, $C_{9-11}$ pareth-3, $C_{11-15}$ pareth-5, $C_{11-15}$ pareth-12, $C_{12-13}$ pareth-2, $C_{12-13}$ pareth-10, $C_{12-13}$ parenth-15, deceth-4, deceth-5, deceth-6, di-$C_{12-13}$ pareth-6 phosphate, di-$C_{12-15}$ pareth-8 phosphate, glyceryl cocoate, glyceryl laurate, glyceryl oleate, isoceteth-10, isodeceth-6, isosteareth-10, laureth-4, laureth-5, laureth-10, octyldodeceth-10, octyldodeceth-20, oleoyl ethyl glucoside, oleth-2, oleth-4, PEG-8 caprate, PEG-8 castor oil, PEG-7 cocamide, PEG-11 cocamide, PEG-15 cocoate, PEG-20 dilaurate, PEG-32 dilaurate, PEG-8 dioleate, PEG-2 distearate, PEG-8 distearate, PEG-8 glyceryl laurate, PEG-15 glyceryl laurate, PEG-4 isostearate, PEG-4 laurate, PEG-5 octanoate, PEG-9 oleamide, PEG-5 oleate, PEG-20 palmitate, PEG-6 stearate, PEG-16 tallate, polysorbate 20, polysorbate 80, steareth-10, trideceth-5, undeceth-9, and mixtures thereof. In yet other preferred embodiments, the composition is emulsified into a microemulsion or is clear. In a preferred embodiment of the invention, the amount of the compound of formula (I) and/or (II) is about 5 wt. % to about 50 wt. % of the formulation, the amount of solvatrope or coupling agent is about 2 wt. % to about 15 wt. % of the formulation, and the amount of oil or hydrophobic organic component is about 5 wt. % to 50 wt. % of the formulation.

For individual applications, the surfactants, viscosity regulators, preservatives, corrosion inhibitors, dyes, perfumes, plant extracts or other additives customary in the respective fields can be used. These agents are sufficiently known to the person skilled in the art from current practice and the corresponding specialist literature and require no further explanation. Many other optional additives are set forth below.

It can be seen from the above, that ranges in amounts given for each ingredient or component of a composition or formulation set forth herein in certain circumstances may be theoretically capable of adding up to a sum of greater than 100%. As would be appreciated by those of skill in the art, it is understood that such impossible formulations (that is, those formulations whose component amounts add to a sum greater than 100%) are excluded from the claims and disclosure. For example, a formulation having components A and B, where the amount of A is said to range from 25% to 75% and the amount of B is said to range from 25% to 55%, if containing 65% of A, is understood to have 35% or less of B in that formulation, so that the sum of A and B does not exceed 100%. Thus, all formulations or compositions presented herein whose component amounts add to a sum less than or equal to 100% are understood as being part of the claims and disclosure.

DETAILED DESCRIPTION OF THE INVENTION

The instant invention relates to a process of making novel tertiary amine esters of general formula (I) and the corresponding protonated or quaternized derivative thereof of general formula (II), the compounds themselves, formulations of the compounds, and their many applications. The invention is described in more detail below.

A. SYNTHESIS

The process of the instant invention involves the following steps:

(a) reacting a ketone or aldehyde having the formula

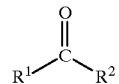

with a glycol to form a ketal or acetal;
(b) reacting the ketal or the acetal with acrylonitrile to form an ether nitrile;
(c) reducing the ether nitrile to a tertiary amine ketal or tertiary amine acetal;
(d) hydrolyzing the tertiary amine ketal or the tertiary amine acetal to a tertiary amine diol;
(e) esterifying the tertiary amine diol to a tertiary amine ester of general formula (I); and, optionally (f) quaternizing the tertiary amine ester of the general formula (I) to the quaternary amine ester of general formula (II).

Although detailed synthesis procedures for each of these steps are set forth below in detail, it should be understood that all of these procedures are exemplary and the invention is not limited to the examples set forth below. As would be appreciated by those of skill in the art, many different synthesis, separation, and analysis methods and different apparatus and equipment are known to those of skill in the art which would produce similar or the same results are the exemplary procedures and methods used below. It is therefore, expected that the exemplary procedures set forth below may be modified, supplemented, or substituted with other methods known to those of skill in the art without departing from the spirit of the invention or the disclosure herein. All such procedures and methods are intended to be covered by the appended claims.

(a) Formation of the Ketal or the Acetal From the Ketone or the Aldehyde and Glycol The general reaction (1) for forming the ketal or the acetal from a ketone or aldehyde of formula $R^1(CO)R^2$ and glycol is shown below.

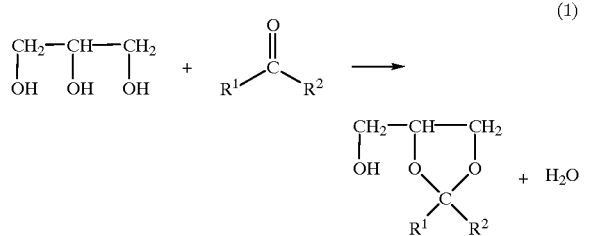

The ketal formation reaction from ketones is similar to the more familiar esterification reaction of aldehydes, although the reaction is more difficult with ketones, see, for example, J. March, *Advanced Organic Chemistry: Reactions, Mechanisms and Structure*, (McGraw-Hill: 1968) pp. 661–662. Therefore, the ketal reaction is preferably performed as a reflux reaction and/or the by-product water is removed during reaction to drive the equilibrium to the products. Hypophosphorous acid (HPPA) is preferably added to maintain the color during the reaction. Catalysts such as oxalic acid and sulfuric acid are also used. Although glycerol is used here, glycerol is only exemplary, and any triol where the hydroxyls are either 1,2 or 1,3 may be substituted therefor. The ketone or the aldehyde $R^1(CO)R^2$ is preferably used in stoichiometric excess of the amount of glycerol or triol used, as before, to drive the equilibrium to the products. In the reaction, water is produced as a by-product that comes over during the reaction along with unreacted ketone or is otherwise removed. Preferably, the ketone or the aldehyde is then recycled back into the reactor. In general, the reaction is performed under atmospheric conditions with a nitrogen sparge. Under such conditions, a cold trap condenser is necessary to keep the ketone or the aldehyde from becoming volatile.

Although any ketone or aldehyde of formula $R^1(CO)R^2$, where $R^1$ and $R^2$ are each independently is hydrogen or a linear, branched, or cyclic alkyl, alkylene, alkaryl, or aryl-containing group containing 1 to 18 carbon atoms, may be used, preferred ketones include acetone, cyclohexanone, 2-pentanone, methyl ethyl ketone, and 2-hexanone, and the most preferred ketone is methyl isobutyl ketone (MIBK), and preferred aldehydes are butyraldehyde (butanal), isobutyraldehyde (2-methylpropanal), n-valeraldehyde, caproaldehyde (hexanal), octanal, decanal, dodecanal, 2-ethylhexanal, and benzaldehyde. MIBK has a boiling point of 117° C.–118° C. at atmospheric conditions. Typical charges for a batch might be as follows: MIBK (55.6 wt. %); glycerol (44.4 wt. %); oxalic acid (0.2 wt. %); sulfuric acid (0.05 wt. %); and 50% HPPA (0.10 wt. %). The glycerol ketal of acetone (commonly called "solketal") has been known for many years and is commercially available.

A typical and preferred reaction procedure for this step is as follows. To a clean reactor, charge all raw materials; start agitation and a nitrogen sparge and agitate without heat for 20 minutes to purge the air out of the reactor. After a 20 minute sparge, start the heat, setting the temperature to 170° C. Initially, the reaction temperature will be about 115° C.–120° C.; however, as the amount of ketone declines and the amount of ketal rises, the reactor temperature will rise. In general, constant heating is necessary in order to keep the reaction going. Generally, the reaction is followed using analytical procedures known by those of skill in the art, for example, gas chromatography (GC). If GC is used, a representative sample is withdrawn from the reactor and the sample is derivatized with trimethylchlorosilane (TMCS) and bis(trimethylsilyl)trifluoroacetamide (BSTFA) before being injected into the GC. Samples after would typically be taken after four hours, then every hour thereafter. The reaction is considered complete when a desired end-point is reached, for example, when there is less than 2% free glycerin.

Once the reaction is completed, the excess ketone is removed. A preferred procedure would be to cool the reactor to below 100° C. while continuing the nitrogen sparge; when the temperature reaches 100° C., a vacuum is applied to the reactor until a pressure of about 150 mmHg (1.98 kPa) is reached; at this point the reactor is heated slowly to 130° C. and the vacuum is increased to about 100 mmHg (1.33 kPa), which should be sufficient to remove the ketone or the aldehyde from the reactor. As noted previously, a cold condenser is needed to trap the ketone or the aldehyde, otherwise, the ketone or the aldehyde will volatilize and cannot be reused. A distillation column with the appropriate number of plates may also be required to separate the ketone or the aldehyde from the ketal or the acetal product. Using such a distillation column, the first 80% of the ketone or the aldehyde removed will contain very little ketal product, however, the last 20% is being removed, the ketal or the acetal product will be found in the ketone or the aldehyde. Once the ketone or the aldehyde has been removed, the reactor is cooled down under vacuum and the vacuum is then broken with a nitrogen sparge. Before the next step, the acids in the ketal or the acetal product will have to be neutralized with an equivalent molar quantity of dry sodium hydroxide or potassium hydroxide (no water is to be used). This step provides about 84% of the theoretical yield of ketal.

(b) Formation of the Ether Nitrile From the Ketal or the Acetal and Acrylonitrile The general reaction (2) for forming the ether nitrile from the ketal or the acetal and acrylonitrile is shown below.

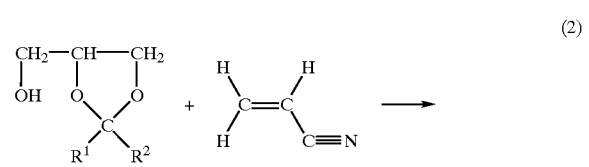

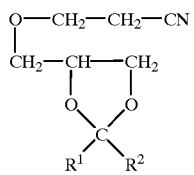

(3)

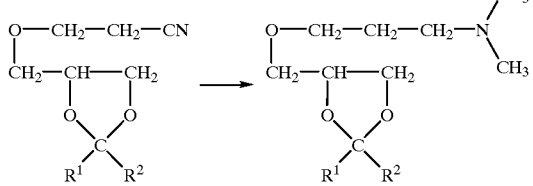

In this step, the ketal or the acetal obtained from the prior step is reacted with acrylonitrile with a strong base catalyst to form the ether nitrile. Subsequently, the catalyst is neutralized with a slight excess of sulfuric acid to prevent the reverse reaction and the excess acid is neutralized with triethanolamine (TEA) to minimize polymerization of the ether nitrile product. Preferably, the crude ether nitrile product is then fractionally distilled under vacuum to make the final purified ether nitrile product.

A typical and preferred reaction procedure is as follows. The reactor to be used and all charge lines to the reactor should be clean and dry. Charge the reactor with the ketal or the acetal, powdered potassium hydroxide, and 25% tetramethylammonium hydroxide in methanol, heating the reactor to 50° C. while stirring the reactants with a slow nitrogen sparge. Once the reactor reaches 50° C., the nitrogen sparge is shut off and a high vacuum (2 mmHg to 5 mmHg (266 Pa to 666 Pa)) is gradually applied to the reactor to distill off the methanol from the catalyst. The high vacuum is maintained until at least 75% of the theoretical methanol has distilled off, at which point the vacuum is broken with a light nitrogen sparge which is maintained. The acrylonitrile is metered in over a 3–6 hour period with the addition rate slowing down as the addition proceeds. This reaction will be exothermic and the temperature should not be allowed to exceed 65° C. After the acrylonitrile addition, the reactor temperature is maintained at 65° C. and samples are taken every hour or two for GC analysis. The reaction is considered complete when a desired end-point is reached, for example, when the amount of free ketal is below 5 wt. % of the reaction mixture. Once the free ketal content is acceptable, sulfuric acid is added to neutralize the base catalyst, after which the stirring of the reaction mixture is maintained for 30 minutes and TEA is added to neutralize any excess sulfuric acid. The stirring of the reaction mixture is maintained for another 30 minutes and then a fractional vacuum distillation of the crude product mixture is prepared.

During fractional vacuum distillation, a vacuum of about 2 mmHg to about 5 mmHg (266 Pa to 666 Pa) is gradually applied to the reactor and the reactor temperature is then raised. For MIBK-derivatives, depending upon the vacuum, the bulk of the forecut will come off between about 65° C. and 120° C. It should amount to 3–6 wt. % of the crude product and can be recycled into the next batch since it consists mostly of the ketal or the acetal starting material. The main fraction will come off between 120° C. and 175° C. and should amount to 85– 95% of the crude product. The residue should amount to 3–10%. Generally, typical charges (assuming the use of MIBK ketal derivative) would be as follows: ketal (76.6 wt. %); acrylonitrile (22.9 wt. %); tetramethylammonium hydroxide (25 wt. % in methanol) (0.4 wt. %); potassium hydroxide (0.1 wt. %); with sulfuric acid and triethanolamine used as needed.

(c) Formation of the Tertiary Amine Ketal or the Tertiary Amine Acetal From the Ether Nitrile The general reaction (3) for forming the tertiary amine ketal or the tertiary amine acetal from the ether nitrile is shown below.

In this step, the ether nitrile is reacted with ammonia and hydrogen in the presence of a catalyst to form the primary amine. The primary amine is then converted into the dimethyl tertiary amine ketal or the dimethyl tertiary amine acetal by adding formaldehyde along with hydrogen. Generally, typical charges (assuming the use of MIBK ether nitrile derivative) would be as follows: MIBK ether nitrile (59.1 wt. %); nickel catalyst available from Activated Metals of Tennessee under the tradename AMCAT 5343 (1.2 wt. %); formaldehyde (37% conc.) (39.7 wt. %); with hydrogen and ammonia used as needed.

The formaldehyde charge is calculated based on the molecular weight of the primary amine, that is, the total amine value (TAV), as follows (56108/TAV). The addition of a greater formaldehyde charge will tend to make the color of the product dark. The full calculation is as follows:

grams of 37% formaldehyde=[grams of ethernitrile×TAV/56108]× [30×2/0.37]

A typical and preferred reaction procedure is as follows. To a clean reactor, charge the ether nitrile and the catalyst, for example, AMCAT 5343 Ni catalyst. The reactants are agitated and a vacuum is applied to 100 mmHg or below while heating is applied to raise the temperature to 40° C. When the reactor reaches 40° C., the reactor is sealed and ammonia is added to achieve a pressure of 90 psig. The reactor is then heated to 120° C., at which point the ammonia pressure is adjusted to 150 psig, and hydrogen gas is subsequently added to achieve a pressure of 600 psig. During this time, the temperature is maintained at 120° C. and the pressure is maintained at 600 psig with the further addition of hydrogen gas. After 2 hours, sample for TAV. For the MIBK ether nitrile, the theoretical TAV for the primary amine is 242.6. The reaction should be continued until a selected end-point is reached; for example, for the MIBK ether nitrile a TAV of 230.5 or higher (95.0% of theoretical) may be considered an appropriate end-point. If TAV is lower than the selected endpoint (for example, 230.5 for the MIBK ether nitrile), the reaction is continued for 30 minutes and rechecked until the selected TAV endpoint is reached. When the TAV endpoint is reached, the hydrogen and ammonia is vented to atmospheric and a vacuum to 100 mmHg or below is applied. The reactor is then sealed and pressurized to 600 psig with hydrogen. The formaldehyde (37% solution) is then added at a constant rate that will allow complete addition of the entire amount over 5 hours. At the conclusion of the formaldehyde addition, the temperature is maintained at 120° C. and 600 psig for 30 minutes, at which point the reactor is cooled to about 75° C. and vented to atmospheric pressure. The reactor contents are then filtered and the recovered crude product, at this point, will be two layers. The layers are allowed to separate and TAV and 3AV (teriary amine value) are measured for the top layer. The tertiary AV (3AV) should be about 90% or more of the TAV. Typical results would be around 174 TAV and 164 3AV. Preferably the bottom layer is retained and used in the hydrolysis step. Lab batches for forming the MIBK tertiary amine ketal have given about 85.1% of the theoretical yield. The major losses of products are likely due to the filtration and vacuum procedures.

(d) Hydrolysis of the Tertiary Amine Ketal or the Tertiary Amine Acetal to the Tertiary Amine Diol The general reaction (4) for forming the tertiary amine ketal or the tertiary amine acetal from the ether nitrile is shown below.

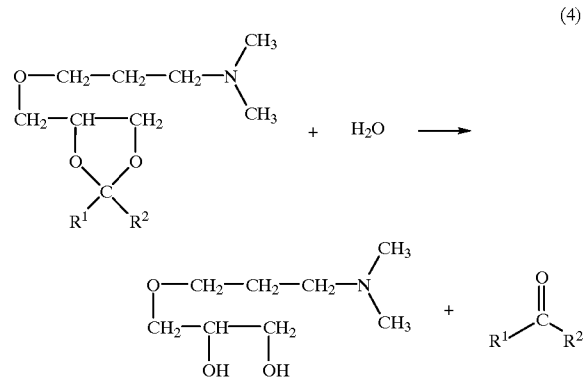

In this step, the tertiary amine ketal or the tertiary amine acetal is hydrolyzed to obtain the tertiary amine diol (hydrolyzed amine). The hydrolysis reaction generally takes place under high temperatures (for example, 175° C.) and acidic conditions. It has been discovered that the acid that yields the highest hydrolysis rate is formic acid and is therefore preferred. Other weak or strong acids, whether organic acids or mineral acids, such as sulfuric, methane sulfonic, and oxalic, may also be used but do not give as high a yield as formic acid. A system of removing and separating the ketone (aldehyde)/water-IPA mixture is necessary to optimize this step.

As noted in the previous step of preparing the tertiary amine ketal or the tertiary amine acetal, water is left in the product. This water, which is not removed, is a large fraction of reaction product mixture of the previous step, typically ranging from 35 wt. % to 50 wt. % of the total reaction product mixture. In this step, the water is used to hydrolyze the tertiary amine ketal or the tertiary amine acetal to the tertiary amine diol. The TAV should be calculated in order to determine the neutralization equivalent (NE). Typically, the number of moles of formic acid added is one-fourth that of the number of moles of tertiary amine ketal or tertiary amine acetal. Generally, typical charges (assuming the use of MIBK ether nitrile derivative) would be as follows: tertiary amine ketal (37.3 wt. %); isopropyl alcohol (IPA) (30.6 wt. %); water (30.6 wt. %); and formic acid (1.5 wt. %).

A typical and preferred reaction procedure is as follows. To a clean reactor, charge all raw materials. The reactants are agitated and a nitrogen purge performed twice. Nitrogen is then added to 50 psig and the absence of leaks confirmed. Such purging of the reactor with nitrogen is necessary to keep the hydrolyzed amine in good color and air must be kept out of the reactor. The nitrogen is vented until a pressure of 20 psig is reached and the reactor is heated to 175° C. Generally, the reaction is followed using analytical procedures known by those of skill in the art, for example, gas chromatography (GC). If GC is used, a representative sample is withdrawn from the reactor and the sample is derivatized with trimethylchlorosilane (TMCS) and bis (trimethylsilyl)trifluoroacetamide (BSTFA) before being injected into the GC. Samples would typically be taken after four hours, then every hour thereafter. The reaction is considered complete when a desired end-point is reached, for example, when the percent of % hydrolyzed material is greater than 98%.

Once the reaction is finished, the water and ketone are removed by cooling the reactor to 80° C. and then applying a vacuum to the reactor until it reaches about 150 mmHg; at this point the reactor is slowly heated to 130° C. and the vacuum is increase to about 85 mmHg. This procedure should be sufficient to remove the ketone or the aldehyde and water from the reactor. It should be noted that a cold condenser is generally needed to trap the MIBK or ketone, which will otherwise volatilize and cannot be reused. A distillation column with the appropriate number of plates may be used to separate the ketone or the aldehyde from the water.

Once the ketone or the aldehyde and water have been removed from the reactor, the reactor is cooled down under vacuum and the vacuum is then broken with a nitrogen sparge. Before the tertiary amine diol can be esterified, it needs to be further purified, for example, by distillation. The MIBK derivative will distill at about 160° C. at 5 mmHg vacuum.

(e) Esterification of the Tertiary Amine Diol to the Tertiary Amine Ester

The general reaction (5) for the esterification of the tertiary amine diol to the tertiary amine ester is shown below.

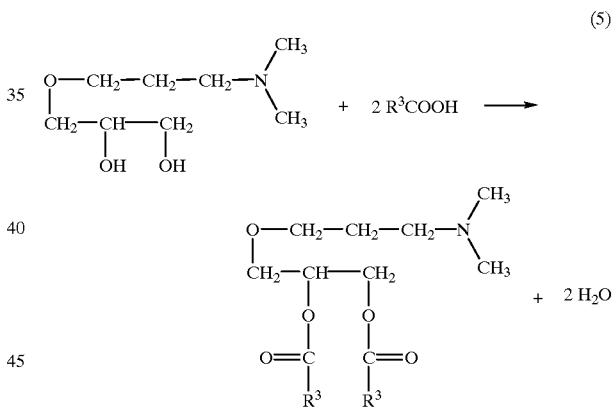

The esterification process can be done under nitrogen sparge at atmospheric conditions or nitrogen sparge under vacuum. Water is the by-product of this reaction and hypophosphorous acid (HPPA) is used as the esterification catalyst. Fatty acids used for the esterification steps are monobasic fatty acids, which may be used in the form of their glycerides, methyl or ethyl esters or as free acids. The extent of unsaturation in these fatty acids or fatty acid esters is, as far as desired, adjusted to a desired iodine value by known catalytic hydrogenation processes, or achieved by mixing fatty components which are completely hydrogenated with fatty components which are not completely hydrogenated. The iodine value (I.V.), a measure of the mean degree of saturation of a fatty acid, is the amount of iodine which is absorbed by 100 grams of the compound to saturate the double bonds. Preferred according to the present invention are tallow fatty acids and palm fatty acids with iodine values between 15 and 50. These are commercially available products and can be obtained from various firms under the respective trade names for these products. According to the invention, preference is given to tallow fatty acids and palm fatty acids having iodine values between 1–50 and rapeseed oil fatty acids having iodine values between 80–120. They are commercially available products and are supplied by various companies under their respective tradenames. A typical charge is as follows: tertiary amine diol (26.2 wt. %); tallow fatty acid (DISTAL 51) (73.6 wt. %); and 50% HPPA (0.2 wt. %). The TAV needs to be determined in order to find the neutralization equivalent, which is needed to charge the proper quantity of amine and fatty acid into the reactor. In addition, the Acid Value (AV) for the desired fatty acid should be determined to ensure accurate charging.

A typical and preferred reaction procedure is as follows. To a clean reactor, charge all raw materials. The reactants are agitated and a nitrogen sparge applied while the reactor is heated and maintained at 185° C. Generally, the reaction is followed using analytical procedures known by those of skill in the art, for example, acid value analysis. Samples would typically be taken after four hours, then every hour thereafter. The reaction is considered complete when a desired endpoint is reached, for example, when the acid value is below ten. If acid value is remaining constant over two samplings, the TAV is measured to determine if enough amine is present. If the TAV is low, additional tertiary amine diol is added; if the TAV is normal, a vacuum may be needed to finish the reaction. Once the acid value is acceptable, the esterification is considered complete and the reactor is cooled to room temperature under a nitrogen sparge.

(f) Protonation or Quaternization of the Tertiary Amine Ester to the Amine Ester Salt or the Quaternary Amine Ester The general reaction (6) for the quaternization of the tertiary amine ester to the quaternary amine ester is shown below.

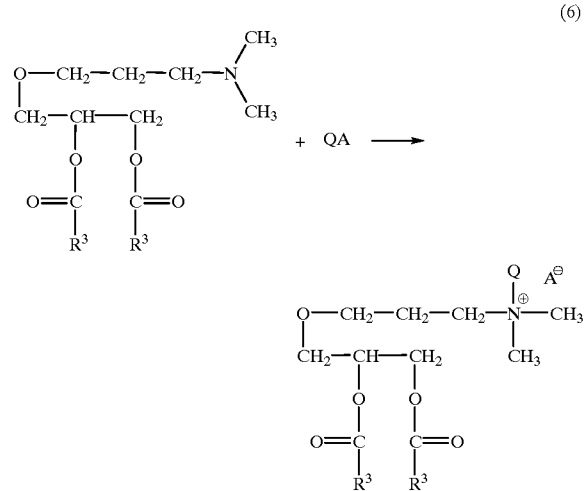

(6)

In this step, which is optional, the tertiary amine ester is protonized (using an acid) or quaternized (using a quaternizing agent) to the respective amine salt or quaternary ammonium compound, respectively. The quaternization is carried out by known processes, generally involving the addition of a slight excess of the quaternizing agent, with stirring and optionally under pressure, to the ester amine, optionally with use of a solvent, preferably isopropanol, ethanol, 1,2-propylene glycol and/or dipropylene glycol, and monitoring completion of the reaction by checking the TAV. Examples of quaternizing agents which can be used are short-chain dialkyl phosphates and sulfates, such as, in particular, dimethyl sulfate (DMS), diethyl sulfate (DES), dimethyl phosphate, diethyl phosphate, and short-chain halogenated hydrocarbons, in particular methyl chloride or dimethyl sulfate. If quaternization is desired, QA represents the quaternizing agent, which may be any quaternizing agent known to those of skill in the art. If protonization is desired, QA may alternatively represent any organic or inorganic acid, that is, Q may be H. In either case, $A^-$ is an inorganic or organic anion. In general, $A^-$, whether shown or understood, may be selected, without limitation, from the group consisting of fluoride, chloride, bromide, iodide, chlorite, chlorate, hydroxide, hypophosphite, phosphite, phosphate, carbonate, formate, acetate, lactate, and other carboxylates, oxalate, methyl sulfate, ethyl sulfate, benzoate, and salicylate, and the like. Preferred examples of the anions are chloride, bromide, methyl sulfate, ethyl sulfate, and salicylate.

A typical and preferred quaternization reaction procedure is as follows. The reactor and all charge lines to the reactor are made clean and dry and the reactor is charged with the required amount of tertiary amine ester and solvent, for example, isopropanol. The reactants are stirred with a slow nitrogen sparge and heated to 50° C., at which point the nitrogen sparge is discontinued and a vacuum is applied to the reactor until the pressure reaches 100 mmHg to 200 mmHg. The molecular weight of the tertiary amine ester should be determined to calculate the proper quantity of quaternizing agent to be used, generally a slight excess. The required amount of quaternizing agent, for example, methyl chloride, is then added. Because the quaternizing reaction is exothermic, the reactor is cooled so that the temperature does not exceed 88° C.–96° C. After the quaternizing agent addition is complete, the reactor is maintained at 90° C. and take a sample every half hour for free amine analysis. The reaction is considered complete when a desired end-point is reached, for example, when the amount of free amine is below 3 wt. % of reaction mixture. Once the free amine content is acceptable, the reactor is cooled to 60° C., at which point a slow nitrogen purge is used to remove excess quaternizing agent, until a desired level is reached. The solvent should be retained until this point is reached and the material must be blanketed with nitrogen as long as it is molten. Generally, typical charges (assuming the use of MIBK tertiary amine ester derivative) would be as follows: MIBK tertiary amine ester (78.6 wt. %); isopropyl alcohol (15.0 wt. %); and methyl chloride (6.4 wt. %).

B. APPLICATIONS

The present disclosure shows that the compounds and formulations of the present invention may be used for many purposes and suitable additives may be incorporated therein based on the ultimate application. Such ingredients, for example, may contribute significantly to the ease of formulation, stability, dispersibility, fluidity, and the performance properties of the compositions.

In one aspect, the present invention provides compounds and formulations that have the ability to impart to fabric (that is, articles of clothing, textiles, and so forth), properties including softness to the touch, ease of handling, increased lubricity, and a reduced tendency to carry or pick tip static electricity. One form in the compounds and formulations of the present invention are provided is as a liquid, for instance, as an emulsion or as a solution/suspension of the desired components. During use, an appropriate controlled amount of the liquid formulation is employed, for example, by pouring the formulation directly into the washing machine. Typically, the formulation is dispensed during the rinse cycle of the washing machine, either poured in by hand or metered in by an appropriate automatic metering device with which the washing machine is equipped.

In addition, the present invention also provides compounds and formulations that may find use as textile treatments to add lubricity and finishing to the fabric prior to shipping the textile to market, particularly when used in conjunction with a resin bath. In such an application, the textile mill would typically apply the formulation in dilute emulsions and rapidly dry the excess water from the fabric to lubricate the fibers and give it a surface finish.

The present invention also provides compounds and formulations that are useful in personal care products such as hair or skin conditioners. In this application, the present invention provides formulations that impart softness, lubricity, and improve the surface appearance of the skin or hair. The hair conditioners additionally reduce the tendency for tangling, improve the manageability, and impart a soft feel to the hair strands. Such hair conditioners are applied as dilute emulsions to the hair following its wash or may be incorporated into a combined conditioner and shampoo composition, also known as a conditioning shampoo, two-in-one shampoo, or two-in-one. Such hair and skin conditioning formulations typically incorporate effective amounts, for example, 0.1 wt. % to 10 wt. % or more, of emollients, humectants, and/or slip and conditioning agents, such as organopolysiloxanes and the like, to create formulations that are monophasic and can be made to be translucent or even clear. Compounds suitable for use as emollients, humectants and conditioners in formulations for skin care or hair care can be found in the CTFA Cosmetic Ingredient Dictionary, 3d Edition, and in the CTFA Cosmetic Ingredient Handbook, which are hereby incorporated by reference in their entireties.

The compositions of the present invention are particularly useful in applications that take advantage of their ability to disperse hydrophobic material, to stabilize foam, and to enhance the penetration and wetting exhibited by the compositions. Examples of such compositions and applications are set forth below, each revealing an additional aspect of the present invention.

The compounds and formulations of the present invention may be used as oil dispersants and oil slick dispersant formulations for application onto oil, for example, onto a film of oil, to disperse the oil.

The compounds and formulations of the present invention may also be used as oil well stimulation and oil recovery aids for injection into oil wells in order to penetrate into the surface of the borehole and assist liberation of crude oil from the matrix material into the borehole, from which it can be brought to the surface.

In addition, the compounds and formulations of the present invention may be used as vehicles for hydrophobic sheeting agents such as mineral oil and silicone oil. Such oils can readily be dispersed in compositions, according to the present invention, and the resulting formulations are highly satisfactory when sprayed or otherwise applied to a surface, such as a freshly washed automobile surface, to impart a lustrous, water-repellent film to the surface.

The compounds and formulations of the present invention may also be used as rinse aids, such as used in automatic dishwashers, wherein application of the composition of the present invention disperses residual hydrophobic matter, including cleaner residues and films.

Furthermore, the compounds and formulations of the present invention may be used as paper deinking and ink flotation agents for treating waste inked paper by addition to the pulp slurry such that the ink is liberated from the paper and prevented from redepositing onto the paper. In this application, the ink is typically dispersed or even fully solubilized in the resulting solution when the ink particles are floated from the fibers.

The compounds and formulations of the present invention may also be used as asphalt emulsion agents for emulsifying finely divided asphalt (at loadings of typically 1–20 wt. %), with or without particulate filler such as sand, in an aqueous phase which comprises the composition according to the present invention.

Moreover, the compounds and formulations of the present invention may be used as corrosion inhibitor agents for application to any surface to which one desires to apply a film that protects against corrosion. The composition would typically contain an effective amount of a hydrophobic corrosion inhibiting material, such as liquid or waxy-solid fatty ester, paraffinic hydrocarbon, silicone, or the like, dispersed in a composition according to the present invention.

In addition, the compounds and formulations of the present invention may be used with ore flotation agents for separating ore from rock. Such floatation agents might include, for example, the agent available from Witco Corporation under the tradename WITCAMINE® AL42-12. Typically, the ore floatation agent (a collector or frother, depending on the characteristics of the particular separation desired in the flotation cell) or mixture thereof, which is a relatively hydrophobic material, is dispersed in a composition according to the invention and an effective amount is added (on a batch or continuous basis) to the ore separation cell. This permits the formulator to improve the dispersibility of the hydrophobic ore floatation agent, which often improves the performance of the mineral separation by improving the efficiency of the floatation agent's dispersibility. This can enable the operator to use smaller amounts of the ore floatation agent to achieve the desired purpose because there is a higher concentration of active ingredients available.

In addition, the compounds and formulations of the present invention may be used as suspension concentrates and emulsifiable concentrates of herbicides, pesticides, miticides, fungicides, or bactericides, wherein one or more liquid or solid, generally hydrophobic, active ingredients are dispersed in a composition according to the present invention. The resulting concentrate can be applied as a concentrate on or around desired vegetation, but is more often mixed with water (for example, at the point of use) to form a final dilute formulation having the desired concentration of active ingredient(s). This application takes advantage of the noteworthy property of this invention that addition of the water does not disrupt the monophasic state, nor the fluidity, of the formulation.

As noted above, the compositions and formulations of the present invention can also optionally contain other components, depending on the additional properties one may wish to provide in the finished composition. Such additional components include, but are not limited to, additional coupling agents and solvents, additional quaternary ammonium compounds, additional surfactants, hydrocarbon actives, perfumes, preservatives including bacteriocides and fungicides, insect and moth repelling agents, polymeric soil release agents, antistatic agents, dyes and colorants, especially bluing agents, viscosity control agents, antioxidants, silicones, defoaming agents, antifoaming agents, emulsifiers, brighteners, opacifiers, freeze-thaw control agents, shrinkage control agents, aloe, humectants, skin protectants, feel modifiers, and mixtures thereof.

Each of the foregoing reactions can be carried out in solvent or in solvent-free conditions, in each case employing conditions well established for the respective reactions in this field.

C. FORMULATIONS AND PROPERTIES

The products as described herein exhibit a number of desirable properties making them particularly suitable for formulation into commercial products such as fabric softeners and other commercial products, as mentioned above.

Most notably, the compounds of formulas (I) and (II) can readily be formulated into useful compositions such as aqueous compositions, which achieve the desired functionality and which are clear, that is, transparent or translucent. This property can be realized at a variety of concentrations of active ingredient, with or even without special solvents or coupling agents. In addition, microemulsion formulations can be made that improve the ease of application and effectiveness of the resulting formulation.

In particular, the compounds of formulas (I) and (II) and their ability to make clear and biodegradable formulation, for example, fabric softeners or personal care formulations, is highly unusual. The compounds of formulas (I) and (II) are most often clear when the iodine value (IV) of the fatty acids used in the esterification is high (about 50 to about 120), for example, canola or oleic fatty acids. The resulting concentrated, clear, and biodegradable formulations have many addvantageous propoerties, depending on the application, for example, such fabric softeners would improve softening, reduce staining, and improve water absorbency over other types of formulations. These new products give good clarity and dispersibility in formulations with solvents selected from a class of C2 to C10 diols, mono-ols, glycol ethers, and esters and/or ester diols. These ester quats can be easily formulated into clear softeners using solvents such as but not limited to: mono-ols C2 to C6 such as IPA, ethanol and propyl alcohol etc., diols of C2 to C10 such as TMPD, and its alkoxylates, hexylene glycol, 2-ethyl-1,3-hexanediol, etc. and ester diols such as hydroxy pivalyl hydroxyl pivalerate (C12 ester diol. Other solvents can include but are not limited to glycol ethers such as propylene glycol n-butyl ether, diethylene glycol n-butyl ether etc. These solvents are added to these unsaturated ester quats (these ester quats are present in the formulation at about 10 to 50% active) at levels between 4 and 50% with the optimum about 8 to 20%. To little solvent and the formulation become thick and opaque and does remain stable. Nonionic and cationic surfactants such as amine ethoxylates, alcohol ethoxylates, and monoalkyl ethoxylated amine quats can be added to improve stability, fluidity and improve dispersibility. Calcium chloride or other salts can be added to thin formulation viscosity and improve stability cost effectively. Salts, both inorganic and organic salts, can be added between 0 to 2% active level. A typical formulation might be:

EXAMPLE A: Fabric Softener

| Component | Amount (weight %) |
| --- | --- |
| Canola/oleic-based soketal ester quat | 40.0 |
| TMPD etoxylate (1 mole) | 11.0 |
| K 205 (Coconut Amine 5 Mole Ethoxylate) 1% | 1.0 |
| Fragrance | 1.5 |
| Calcium chloride | 0.10 |
| Water, 9° German hardness | to 100 |

Emulsion or microemulsion formulations according to the present invention have many applications, for example, as car "cheater" wax spray technology to improve beading and act as a drying aid, as fabric softeners, and as personal care products, for example, as a moisturizer/conditioner if the compound of formulas (I) and/or (II) is not skin irritating. In addition, such emulsions or microemulsions may find uses as emulsifiers for silicone oils and pesticides, and as emulsifiers/softeners for textile finishing. Generally such formulations include three components: (a) compound of formulas (I) and/or (II), (b) a solvatrope or coupling agent and blends thereof, and (c) an oil or hydrophobic organic component and blends thereof, which are blended in water. These microemulsion formulations give stable, clear (translucent) products that do not go through thick or viscous gel phases but disperse readily and quickly into very fine particle size microemulsions when diluted or dispersed in water. These microemulsions have many additional advantages over conventional microemulsions, such as the products sold by Witco Corporation under the tradename CARSPRAY™: reduced particle size, improved beading and sheeting over, and improved biodegradability, especially when used with methyl ester oils.

If the resulting formulation is intended to be used as a personal care formulation, the amount of the compound of formulas (I) and/or (II) is about 0.1 wt. % to about 65 wt. % of the formulation, preferably about 0.1 wt. % to about 25 wt. %, and most preferably about 0.1 wt. % to about 5 wt. %; the amount of solvatrope or coupling agent is about 0.1 wt. % to about 65 wt. % of the formulation, preferably about 0.1 wt. % about 25 wt. %, and most preferably about 0.1 wt. % to about 0.5 wt. %; the amount of oil or hydrophobic organic component is about 0.1 wt. % to 65 wt. % of the formulation, preferably about 0.1 wt. % to about 25 wt. %, and most preferably about 0.1 wt. % to about 5 wt. %; and the amount of water is about 20 to 99.7 wt. % of the formulation, preferably about 35 wt. % to about 99.7 wt. %, and most preferably about 65 wt. % to about 99.7 wt. %.

If the resulting formulation is intended to be used in a car drying aid formulation or other application, the amount of the compound of formulas (I) and/or (II) is about 5 wt. % to about 50 wt. % of the formulation, preferably about 10 wt. % to about 30 wt. %, and most preferably about 15 wt. % to about 25 wt. %; the amount of solvatrope or coupling agent is about 2 wt. % to about 15 wt. % of the formulation, preferably about 3 wt. % about 10 wt. %, and most preferably about 6 wt. % to about 10 wt. %; the amount of oil or hydrophobic organic component is about 5 wt. % to 50 wt. % of the formulation, preferably about 10 wt. % to about 30 wt. %, and most preferably about 15 wt. % to about 20 wt. %; and the amount of water is about 10 to 70 wt. % of the formulation, preferably about 20 wt. % to about 60 wt. %, and most preferably about 30 wt. % to about 50 wt. %.

Although the compounds of formulas (I) and/or (II) have many potential uses, in particular, they exhibit highly satisfactory fabric softening capabilities. Thus, the compounds of formulas (I) and/or (II), as well as mixtures of such compounds, can be advantageously formulated appropriately into products useable as fabric softeners. Preferred emulsions useful as fabric softener compositions can contain about 2 wt. % to about 80 wt. %, preferably 5 wt. % to 30 wt. %, and more preferably 6 wt. % to 25 wt. %, of one or more compounds corresponding to formulas (I) and/or (II). In general, higher solids contents can be provided more easily with lower degrees of quaternization. On the other hand, higher degrees of quaternization (such as a degree of quaternization approaching 2.0 for a diamine), lead to aqueous formulations wherein the maximum acceptable solids content without excessive solubility problems is lower.

The compounds of formulas (I) and/or (II) can be formulated into compositions, including clear fabric softener compositions. Such fabric softening composition would typically include water and one or more of the solvents which are conventionally used in formulating fabric softeners. Examples of such solvents include ethanol, isopropanol, hexylene glycol, propylene glycol, diethylene glycol, or similar solvent of mixture thereof, as a concentrate or more dilute form, depending on the application. Selection of a suitable solvent for a particular application is well-known to those of skill in the art. Such formulations generally comprise about 10 wt. % tip to about 50 wt. % of one compound of formulas (I) and/or (II) or a mixture thereof.

The compounds of formulas (I) and/or (II) can be formulated with greater ease than is encountered with conventional quaternary ammonium fabric softener actives. Most conventional quaternary ammonium compounds exhibit a tendency to form a gel during dilution with water when formulated in clear formulations. When formulated in clear formulations, however, the compounds of formulas (I) and/or (II) show very little gelation, or no gelation at all, during dilution with water, even cold water, which would be expected to provoke gelation. This freedom from a tendency to gel means that compositions including compounds of formulas (I) and/or (II) can be prepared at active concentrations of 40 wt. % or higher, for example, even 50 wt. % or higher. The preparation itself of such formulations is much simpler: the freedom from gelation means that when a formulator chooses to manufacture a more concentrated product for resale to the consumer, there is no need for special treatment to deal with gel formation. Also, the freedom from gel formation means that the consumer can use the more concentrated product directly without concern that a gelled by product would form. For example, the consumer could add a concentrated fabric softener composition according to the present invention directly into the wash water in the wash or rinse cycle, without any apprehension that a gel will form that that would reduce softening efficiency or leave a deposit on the clothes.

It should be noted that the ability of the compounds of formulas (I) and/or (II) to form a clear formulation, at lower and at higher concentrations, extends also to formulations which also contain one or more other quaternary ammonium compounds as fabric softener co-actives, as well as other additives as disclosed herein.

D. ADDITIONAL CONVENTIONAL QUATERNARY AMMONIUM COMPOUNDS

Additional conventional quaternary ammonium compounds or salts may be present with the compound or compounds of formulas (I) and/or (II) in accordance with the present invention. The compounds presented below are only examples of conventional quaternary compounds that are suitable for use in the formulations of the present invention. As with the compounds of formulas (I) and/or (II), these conventional quaternary ammonium compounds (quats or salts) may have an anion to provide electrical neutrality and, in general, such anion may be any anion which is not deleterious to the properties of the overall compound. Thus, in the structural formulas (i) to (xxiii) below, the counteranion, whether designated as $A^-$ or not shown but understood, may be selected, without limitation, from the group consisting of fluoride, chloride, bromide, iodide, chlorite, chlorate, hydroxide, hypophosphite, phosphite, phosphate, carbonate, formate, acetate, lactate, and other carboxylates, oxalate, methyl sulfate, ethyl sulfate, benzoate, and salicylate, and the like. Preferred examples of the anions are chloride, bromide, methyl sulfate, ethyl sulfate, and salicylate. If the anion is monovalent (has a charge of $-1$), $A^-$ represents the anion group, if the anion is divalent (has a charge of $-2$), $A^-$ represents half of the anion group, if the anion is trivalent (has a charge of $-3$), $A^-$ represents a third of the anion group, and so on.

The conventional quats that may be formulated with the compounds of formulas (I) and/or (II) in accordance with the present invention include, but are not limited to, nitrogenous compounds selected from the group consisting of quaternized or acid salt derivatives of:

(i) alkylene diamines, diamides, or amidoamines, including compounds of the formula:

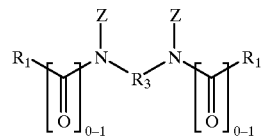

wherein each $R^1$ is an acyclic alkyl or alkylene $C_{12}-C_{21}$ hydrocarbon group, each Z is $-(R_2O)_{0-4}H$, or $-R_2H$, and $R_2$ and $R_3$ are divalent $C_1-C_6$ alkylene groups;

(ii) substituted imidazoline compounds having the formula:

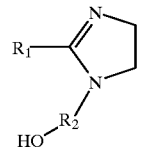

(iii) reaction products of higher fatty acids with alkylenetriamines in, for example, a molecular ratio of about 2:1, the reaction products containing compounds of the formula:

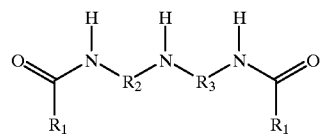

wherein $R_1$, $R_2$ and $R_3$ are defined as above; and (iv) substituted imidazoline compounds having the formula:

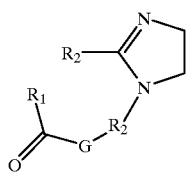

wherein G is —O— or —NH— and $R_1$ and $R_2$ are defined as above; and mixtures thereof.

Preferred examples of compounds of structural formula (i) are those derived from hydrogenated tallow fatty acids and the hydroxyalkylalkylenediamine is N-2-hydroxyethylethylenediamine, such that $R_1$ is an aliphatic $C_{15}$–$C_{21}$ hydrocarbon group, and $R_2$ and $R_3$ are divalent ethylene groups.

A preferred example of a compound of structural formula (iii) is stearic hydroxyethyl imidazoline, wherein $R_1$ is an aliphatic $C_{21}$ hydrocarbon group and $R_2$ is a divalent ethylene group.

A preferred example of compounds of structural formula (iii) is N,N"-ditallowalkanoyidiethylenetriamine where $R_1$ is an aliphatic $C_{15}$–$C_{21}$ hydrocarbon group and $R_2$ and $R_3$ are divalent ethylene groups.

A preferred example of compounds of structural formula (iv) is 1-tallowamidoethyl-2-tallowimidazoline wherein $R_1$ is an aliphatic $C_{15}$–$C_{21}$ hydrocarbon group and $R_2$ is a divalent ethylene group.

Both N,N"-ditallowalkanoyidiethylenetriamine and 1-tallowethylamido-2-tallowimidazoline are reaction products of tallow fatty acids and diethylenetriamine, and are precursors of the cationic fabric softening agent methyl-1-tallowamidoethyl-2-tallowimidazolinium methylsulfate (see "Cationic Surface Active Agents as Fabric Softeners," R. R. Egan, *Journal of the American Oil & Chemicals Society*, January 1978, pages 118–121). N,N"-ditallowalkanoyldiethylenetriamine and 1-tallowamidoethyl-2-tallowimidazoline can be obtained from Witco Corporation. Methyl-1-tallowamidoethyl-2-tallowimidazolinium methylsulfate is available from Witco Corporation under the tradename VARISOFT® 475.

Other suitable quats are those containing one long chain acyclic aliphatic $C_8$–$C_{22}$ hydrocarbon group, selected from the group consisting of:

(v) acyclic quaternary ammonium salts having the formula:

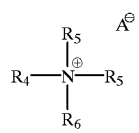

wherein $R_4$ is an acyclic aliphatic $C_8$–$C_{22}$ hydrocarbon group, alkyl, benzyl or ($C_4$–$C_{18}$ alkyl)-$(OCH_2CH_2)_{2-3}$-, $R_5$ and $R_6$ are $C_1$–$C_4$ saturated alkyl or hydroxyalkyl groups, and $A^-$ is an anion as defined above;

(vi) substituted imidazolinium salts having the formula:

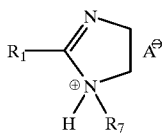

wherein $R_1$ is an acyclic alkyl or alkylene $C_{12}$–$C_{21}$ hydrocarbon group, $R_7$ is hydrogen or a $C_1$–$C_4$ saturated alkyl or hydroxyalkyl group, and $A^-$ is an anion as defined above;

(vii) substituted imidazolinium salts having the formula:

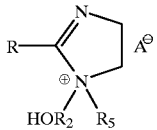

wherein $R_1$, $R_2$, $R_5$, and $A^-$ are as defined above;

(viii) alkylpyridinium salts having the formula:

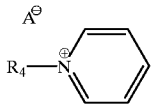

wherein $R_4$ is an acyclic aliphatic $C_8$–$C_{22}$ hydrocarbon group and $A^-$ is an anion as defined above; and (ix) alkanamide alkylene pyridinium salts having the formula:

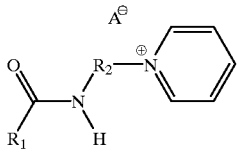

wherein $R^1$ is an acyclic aliphatic $C_{12}$–$C_{21}$ hydrocarbon group, $R_2$ is a divalent $C_1$–$C_6$ alkylene group, and $A^-$ is an anion as defined above; and mixtures thereof.

Examples of compounds of structural formula (v) are the monoalkyltrimethylammonium salts including monotallowtrimethylammonitim chloride, mono(hydrogenated tallow)-trimethylammonium chloride, palmityltrimethylammonium chloride and soyatrimethylammonium chloride, available from Witco Corporation under the tradenames ADOGEN® 471, ADOGEN® 441, ADOGEN® 444, and ADOGEN® 415, respectively. In these compounds, $R_4$ is an acyclic aliphatic $C_{16}$–$C_{18}$ hydrocarbon group, and $R_5$ and $R_6$ are methyl groups. In this application, mono(hydrogenated tallow)trimethylammonium chloride and monotallowtrimethylammonium chloride are preferred. Other examples of compounds of structural formula (v) are behenyltrimethylammonium chloride wherein $R_4$ is a $C_{22}$ hydrocarbon group, which is available from the Humko Chemical Division of Witco Corporation under the tradename KEMAMINE® Q2803-C; soyadimethylethylammonium ethylsulfate wherein $R_4$ is a $C_{16}$–$C_{18}$ hydrocarbon group, $R_5$ is a methyl group, $R_6$ is an ethyl group, and $A^-$ is an ethylsulfate anion; and methyl bis(2-hydroxyethyl) octadecylammonium chloride wherein $R_4$ is a $C_{18}$ hydrocarbon group, $R_5$ is a 2-hydroxyethyl group and $R_6$ is a methyl group.

An example of a compound of structural formula (vii) is 1-ethyl-1-(2-hydroxyethyl)-2-isoheptadecylimidazolinium ethylsulfate wherein $R^1$ is a $C_{17}$ hydrocarbon group, $R_2$ is an ethylene group, $R_5$ is an ethyl group, and $A^-$ is an ethylsulfate anion.

Other quats useful in the present invention include cationic nitrogenous salts having two or more long chain acyclic aliphatic $C_8$–$C_{22}$ hydrocarbon groups or one long chain acyclic aliphatic $C_8$–$C_{22}$ hydrocarbon group and an arylalkyl group. Examples include:

(x) acyclic quaternary ammonium salts having the formula:

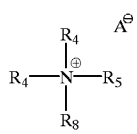

wherein each $R_4$ is an acyclic aliphatic $C_8$–$C_{22}$ hydrocarbon group, $R_5$ is a $C_1$–$C_4$ saturated alkyl or hydroxyalkyl group, $R_8$ is selected from the group consisting of $R_4$ and $R_5$ groups, and $A^-$ is an anion as defined above;

(xi) diamido quaternary ammonium salts having the formula:

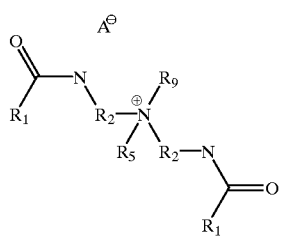

wherein each $R_1$ is an acyclic alkyl or alkylene $C_{12}$–$C_{21}$ hydrocarbon group, each $R_2$ is a divalent alkylene group having 1 to 3 carbon atoms, $R_5$ and $R_9$ are $C_1$–$C_4$ saturated alkyl or hydroxyalkyl groups, and $A^-$ is an anion as defined above;

(xii) alkoxylated diamido quaternary ammonium salts having the formula:

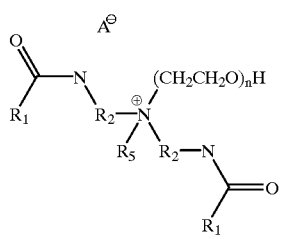

wherein n is equal to 1 to about 5, and $R_1$, $R_2$, $R_5$, and $A^-$ are as defined above;

(xiii) quaternary ammonium compounds having the formula:

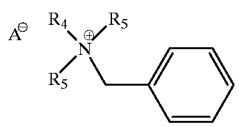

wherein $R_4$ is an acyclic aliphatic $C_8$–$C_{22}$ hydrocarbon group, each $R_5$ is a $C_1$–$C_4$ saturated alkyl or hydroxyalkyl group, and $A^-$ is an anion as defined above;

(xiv) amide-substituted imidazolinium salts having the formula:

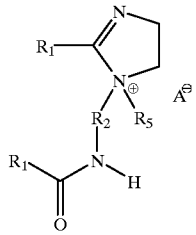

wherein each $R_1$ is an acyclic aliphatic $C_{12}$–$C_{21}$ hydrocarbon group, $R_2$ is a divalent alkylene group having 1 to 3 carbon atoms, and $R_5$ and $A^-$ are as defined above, or $R_5$ is —H; and (xv) ester-substituted imidazolinium salts having the formula:

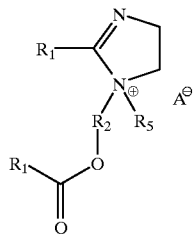

wherein $R_1$, $R_2$, $R_5$, and $A^-$ are as defined above; and mixtures thereof.

Examples of compounds of structural formula (x) are the well-known dialkyldimethylammonium salts including ditallowdimethylammonium chloride, ditallowdimethylammonium methylstilfate, distearyldimethylaminonium chloride, di(hydrogenated tallow)dimethylammonium chloride, dibehenyidimethylammonium chloride. Di(hydrogenated tallow)dimethylammonium chloride and ditallowdimethylammonium chloride are preferred. Examples of commercially available dialkyldimethylammonium salts usable in the present invention are di(hydrogenated tallow)dimethylammonium chloride (available from Witco Corporation under the tradename ADOGEN® 442); ditallowdiinethylammonium chloride (available from Witco Corporation under the tradename ADOGEN® 470); distearyidimethylammonium chloride (available from Witco Corporation under the tradename AROSURF® TA-100); dicocodimethyl ammonium chloride (available from Witco Corporation under the tradename ADOGEN® 462), and dibehenyidimethylammonium chloride, wherein $R_4$ is an acyclic aliphatic $C_{22}$ hydrocarbon group (available from the Humko Chemical Division of Witco Corporation under the tradename KEMAMINE® Q-2802C).

Examples of compounds of structural formula (xi) are methylbis(tallowamidoethyl)(2-hydroxyethyl)ammonium methylsulfate and methylbis(hydrogenatedtallowamidoethyl)(2-hydroxyethyl) ammonium methylsulfate, wherein $R_1$ is an acyclic aliphatic $C_{15}$–$C_{17}$ hydrocarbon group, $R_2$ is an ethylene group, $R_5$ is a methyl group, $R_9$ is a hydroxyalkyl group and $A^-$ is a methylsulfate anion; both of these materials are available from Witco Corporation under the tradenames VARISOFT® 222 and VARISOFT® 110, respectively.

An example of a compound of structural formula (xiii) is dimethylstearylbenzylammonium chloride, wherein $R_4$ is an acyclic aliphatic $C_{18}$ hydrocarbon group, $R_5$ is a methyl group and $A^-$ is chloride, which is available from Witco Corporation under the tradename VARISOFT® SDC.

Examples of compounds of structural formula (xiv) are 1-methyl-1-tallowamidoethyl-2-tallowimidazolinium methylsulfate and 1-methyl-1-(hydrogenated tallowamidoethyl)-2-(hydrogenated tallow)imidazolinitim methylsulfate wherein $R_1$ is an acyclic aliphatic $C_{15}$–$C_{17}$ hydrocarbon group, $R_2$ is an ethylene group, $R_5$ is a methyl group and $A^-$ is a chloride anion; available from Witco Corporation under the tradenames VARISOFT® 475 and VARISOFT® 445, respectively.

Additional examples of quaternary ammonium compounds useful in the present invention include:

(xvi) compounds having the formula:

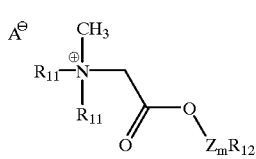

wherein $R_{11}$ is selected from the group consisting of:
(a) —$CH_3$, —$CH_2CH_3$, —$CH_2CH_2OH$, or straight chain aliphatic hydrocarbon groups each of which contains from 12 through 24 carbon atoms, (b) ether groups each of which has the structure: $R_{13}O(CH_2O)_y$—, (c) amide groups each of which has the structure:

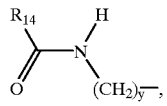

and (d) ester groups each of which has the structure:

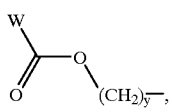

$R_{12}$ is a straight chain aliphatic hydrocarbon group containing from 8 to 32 carbon atoms, $R_{13}$ is a straight chain aliphatic hydrocarbon group containing from 8 to 21 carbon atoms, $R_{14}$ is a straight chain aliphatic hydrocarbon group containing from 7 to 17 carbon atoms, Z is an alkoxy group containing one oxygen atom and either two or three carbon atoms, $A^-$ is an anion as defined above, m is an integer from 1 through 12, and y is an integer which is either 2 or 3.

Yet additional examples of fabric softening compounds useful in the present invention include:

(xvii) compounds having the formula:

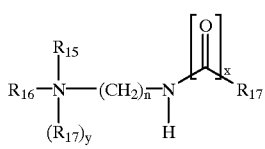

wherein $R_{15}$ is hydrogen or $C_1$–$C_4$ alkyl,

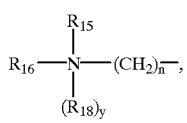

each $R_{16}$ is $C_1$–$C_4$ alkyl or each $R_{17}$ is a $C_8$–$C_{28}$ alkyl or alkenyl group, $R_{18}$ is hydrogen or $C_1$–$C_4$ alkyl, each y is 0 or 1, x is 0 or 1, and each n is from 1 to 6;

(xviii) amides represented by the structural formula:

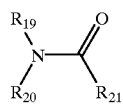

wherein $R_{19}$ and $R_{20}$ are selected independently from the group consisting of $C_{1-22}$ alk(en)yl aryl or alkyl aryl groups, $R_{21}$ is hydrogen or a $C_{1-22}$ alk(en)yl, aryl or alkyl-aryl group or is O—$R_{22}$, wherein $R_{22}$ is a $C_{1-22}$ alk(en)yl, aryl or alkyl-aryl group, and $R_{21}$ and $R_{22}$ optionally contain 1 to 10 alkylene oxide units or functional groups selected from hydroxy, amine, amide, ester, and ether groups; the aryl groups being possibly derived from heterocyclic compounds; at least one of the $R_{19}$ and $R_{20}$ groups contains 10 or more carbon atoms; and where the sum of carbon atoms in $R_{19}$+$R_{20}$+$R_{21}$ is equal to or greater than 14. Preferably, the sum of carbon atoms in $R_{19}$+$R_{20}$ is equal to or greater than 16. Examples of compounds of structural formula (xviii) include N,N-ditallow acetamide, N,N-dicoconut acetamide, N,N-dioctadecyl propanamide, N-dodecyl-N-octadecyl acetamide, N-hexadecyl-N-dodecyl butanamide, N,N-ditallow benzamide, N,N-dicoconut benzamide, and N,N-ditallow 2-phenyl acetamide.

Additional fabric softening compounds useful in the present invention include all ester quaternaries, including but not limited to:

(xix) compounds of the following structural formulas:

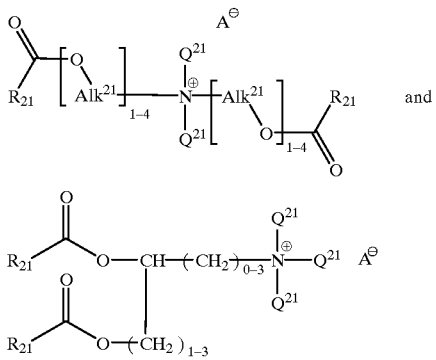

wherein
each $R_{21}$ is independently a saturated or unsaturated alkyl or alkylene radical containing 12 to 22 carbon atoms;
each $Q^{21}$ is independently an alkyl group containing 1 to 4 carbon atoms, benzyl, —$CH_2CH_2OH$, —$CH_2CH(OH)CH_3$, or $R_{21}$—C(O)—(O-(Alk$^{21}$))$_{1-4}$-;
each Alk$^{21}$ is independently $C_2H_4$, $C_3H_6$ or $C_4H_8$; and
$A^-$ is an anion as defined above;

(xx) compounds of the formula:

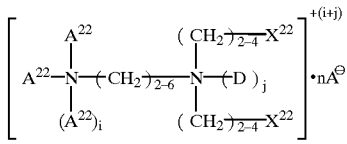

wherein
each $A^{22}$ is the same or different and each is alkyl containing up to 3 carbon atoms, benzyl, or H-(Alk$^{22}$-O)$_{1-3}$-Alk$^{22}$- wherein each Alk$^{22}$ signifies —$CH_2CH_2$—, —$CH(CH_3)CH_2$—, or —$CH_2CH(CH_3)$—, provided further that one of the $A^{22}$ can be hydrogen;
D is methyl, ethyl, propyl, —(CH$_2$)$_{1-3}$COO—, benzyl or hydrogen;
i is 0 or 1 and j is 0 or 1, provided that the sum of (i+j) is 1 or 2;
each $X^{22}$ is a straight or branched saturated or unsaturated aliphatic group containing up to 3 carbon-carbon double bonds and containing 11 to 23 carbon atoms;
n is two minus the number of —(CH$_2$)$_{1-3}$COO— substituents present; and
$A^-$ is an anion as defined above;

(xxi) compounds of the formula:

$R_{23}$—[C(O)O(CH$_2$)$_{1-5}$]$_{0-1}$—C(O)NH(CH$_2$)$_{2-5}$—N(R$_{23a}$)(R$_{23b}$)—(CH$_2$)$_{2-5}$—OC(O)R$_{23}$A$^-$ wherein
each $R_{23}$ is independently straight or branched alkyl or alkenyl containing 8 to 22 carbon atoms;
$R_{23a}$ is straight or branched alkyl or hydroxyalkyl containing 1 to 3 carbon atoms, benzyl, or —$C_2H_4OC(O)R_{26}$, wherein $R_{26}$ is straight or branched alkyl or alkenyl containing 8 to 22 carbon atoms;

$R_{23b}$ is —H, —$CH_3$, —$C_2H_5$ or benzyl; and
$A^-$ is an anion as defined above; and (xxii) compounds of the following structural formulas:

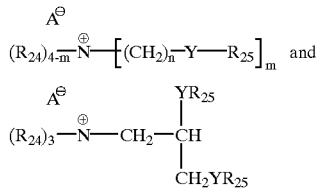

wherein
each $R_{24}$ is independently straight or branched alkyl or alkenyl containing 1 to 8 carbon atoms and 0 to 3 hydroxyl groups;
each $R_{25}$ is straight or branched alkyl or alkenyl containing 10 to 22 carbon atoms and 0 to 3 hydroxyl groups;
each Y is —O—C(O)— or —C(O)—O—;
each m is 1 to 3;
each n is from 1 to 8; and
$A^-$ is an anion as defined above.

Preferred examples of compounds of structural formulas (xxii) include methyl diethanolamine (MDEA) ester quats, triethanolamine (TEA) ester quats, for example, di-(tallow carboxyethyl)hydroxyethyl methylammonium methosulfate, available from Witco Corporation under the tradename REWOQUAT® WE 16, or epichlorohydrin-based ester quats, all of which are used and accepted as fabric softeners worldwide because of their favorable biodegradation profiles, but usually lack the optimum softening performance of other quats.

Additional compounds useful in the present invention include polyester polyquaternary compounds, including but not limited to:

(xxiii) compounds of the following structural formula:

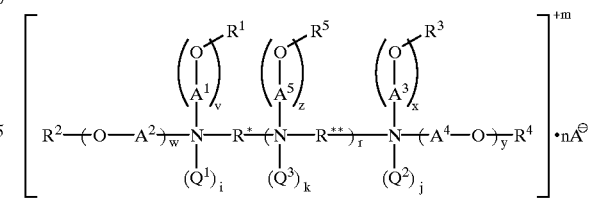

wherein
each of R* and R** is independently a linear, branched or cyclic alkylene group containing 2 to 12 carbon atoms, wherein no two nitrogen atoms are separated by fewer than 2 carbon atoms;
each of $A^1$, $A^2$, $A^3$, $A^4$, and $A^5$ is independently a straight or branched alkylene containing 2 to 4 carbon atoms;
each of $R^1$, $R^2$, $R^3$, $R^4$, and $R^5$ is independently —H or $R^AC(O)$— wherein $R^A$ is straight or branched alkyl or alkenyl containing 7 to 21 carbon atoms and 0 to 4 carbon-carbon double bonds; provided that at least one of $R^1$, $R^2$, $R^3$, $R^4$, or $R^5$ is $R^AC(O)$—;
each of $Q^1$, $Q^2$ and $Q^3$ is independently —H, $CH_3$, —$C_2H_5$, —$C_3H_7$, —$C_4H_5$, benzyl, —$CH_2COOH$, or —$CH_2COOA^-$; or, if R* is a —$CH_2CH_2$— group, $Q^1$ and $Q^3$ together or $Q^1$ and $Q^2$ together may be a —$CH_2CH_2$— group to form a six-membered piperazine ring; or, if R** is a —CH₂CH₂— group, Q³ and Q³ together may be a —CH₂CH₂— group to form a six-membered piperazine ring;

m is 0 to 4;

r is 0 to 2;

each of v, w, x, y, and z is independently 1 to 8;

i is 0 to 1, j is 0 to 1, and each k is 0 to 1, and the sum of (i+j+k) is 0 to 4;

each A⁻ is independently an anion that may be selected, without limitation, from the group consisting of fluoride, chloride, bromide, iodide, chlorite, chlorate, hydroxide, hypophosphite, phosphite, phosphate, carbonate, formate, acetate, lactate, and other carboxylates, oxalate, methyl sulfate, ethyl sulfate, benzoate, and salicylate, and the like; and n is the number of moles of A⁻ needed to give the compound of structural formula (xxiii) a zero net charge. Compounds of structural formula (xxiii), formulations thereof, and uses thereof, form the subject matter of pending U.S. application Ser. No. 09/170,623, filed on Oct. 13, 1998, which is incorporated by reference in its entirety; and (xxiv) compounds of the following structural formulas:

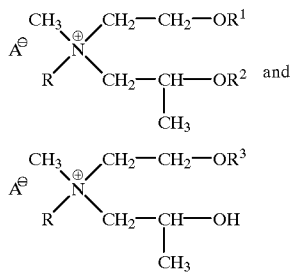

wherein

R is —H, —CH₃ or —C₂H₅;

R¹, R², and R³ are each independently of one another fatty acid radicals having 6–22 carbon atoms; and A⁻ is an inorganic or organic anion that may be selected, without limitation, from the group consisting of fluoride, chloride, bromide, iodide, chlorite, chlorate, hydroxide, hypophosphite, phosphite, phosphate, carbonate, formate, acetate, lactate, and other carboxylates, oxalate, methyl sulfate, ethyl sulfate, benzoate, and salicylate, and the like. Compounds of structural formula (xxiv), formulations thereof, and uses thereof, form the subject matter of pending PCT application No. PCT/US99/00213, filed on Jan. 6, 1999 and pending PCT application No. PCT/US99/00295, filed on Jan. 7, 1999, both of which are incorporated by reference in their entireties.

E. DIOL AND DIOL ALKOXYLATE COUPLING AGENT ADDITIVES

In a preferred embodiment of this invention, fabric softener formulations and other formulations which may be clear (translucent or transparent) and easily dispersed in water can be provided by including an appropriate amount of one or more straight or branched alkyl diols containing 4 to 12 carbon atoms, and/or alkoxylates of such diols with up to 40 alkoxy units per diol moiety, wherein the alkoxylate chains are composed of alkoxy units which are ethoxy, propoxy or butoxy or mixtures thereof, and preferably ethoxy or propoxy. These diol and diol alkoxylate hydrotropes or coupling agents are added to the formulations to increase the amount of the relatively water-insoluble surfactants that can be solubilized into the system. In most cases, they do not act as surfactants to lower surface tension but they often allow surfactants in the presence of salts or electrolytes to be added and subsequently dispersed into water at higher concentrations or at lower viscosities of the formulation than is otherwise achieved using only surfactant and water. These coupling agents assist surfactants by increasing the surfactant's solubility in water and its stability in the formulation, especially in the presence of salts, electrolytes and/or pH agents.

These diols and alkoxylates correspond to structural formula (T)

$$HO-(X-O)_x-R^T-(O-Y)_y-OH \qquad (T)$$

wherein each X and each Y is ethylene (that is, —C₂H₄—), propylene (that is, —C₃H₆—), or butylene (that is, —C₄H₈—); x is 0–40; y is 0–40; the sum (x+y) is 0–40; and $R^T$ is straight, branched or cyclic alkyl containing 4 to 12 carbon atoms. Preferably, $R^T$ contains 7–12 or even 7–9 carbon atoms.

The alkylene residue $R^T$ in structural formula (T) represents a saturated, straight-chain, branched-chain, or cyclic moiety containing 4 to 12 carbon atoms. It is preferred that $R^T$ is branched, wherein the term "branched" is intended to encompass structures having one side alkyl chain, more than one side alkyl chain, or one or more side alkyl chains, one or more of which is itself branched. Branched structures include cyclic structures substituted with one or more alkyl groups, the alkyl groups being straight or branched. Examples of suitable $R^T$ groups include such groups as —CH₂CH(CH₃)CH₂—, —(CH₂)₆—, —CH₂CH₂CH₂—, —C(CH₃)₂CH₂—, —CH₂CH(CH₂CH₃)CH₂CH₂CH₂CH₂—, —CH₂C(CH₃)₂CH₂—CH₂C(CH₃)₂CH(CH(CH₃)₂)₂—, —CH₂CH(CH₂CH₂CH₂CH₃)—, and

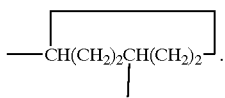

In the alkoxylated diols, the number of repeating units in each poly(alkoxy) chain can be up to 40 but it is preferred that each chain contains 1 to 10 repeating alkoxy units or more preferably 1 to 5 alkoxy units. The preferred alkoxy chains are poly(ethoxy), or are composed of 1 to 2 ethoxy units capped with a chain of 1 to 5 propoxy units.

Compounds of structural formula (T) defined above are in many instances commercially available. Compounds of structural formula (T) can be prepared in straightforward manner familiar to those of ordinary skill in this art by obtaining or preparing the corresponding precursor diol of structural formula HO—$R^T$—OH, and then alkoxylating the precursor diol with a stoichiometrically appropriate number of moles of the desired corresponding alkylene oxide, such as ethylene oxide, propylene oxide, and/or butylene oxide. In those cases where it is desired to alkoxylate only one of the hydroxyl groups on the precursor diol, in some embodiments the alkoxylation will preferentially occur at only one of the hydroxyl groups, particularly where one of them is a primary hydroxyl and the other is a secondary hydroxyl. However, in those cases where both hydroxyl groups on the precursor diol might tend to alkoxylate but alkoxylation at only one of the hydroxyl groups is desired, the hydroxyl group at which alkoxylation is desired not to occur can be protected by preliminarily reacting it with a suitable protecting group such as a lower alkyl moiety or an esterifying substituent. Thereafter, following the alkoxylation, the protecting group is removed in a known manner.

Preferred examples of compounds of the foregoing structural formula (T) include any one, or mixtures, of 2,2,4-trimethyl-1,3-pentanediol (TMPD) and/or 2-ethylhexane-1,3-diol, and/or the reaction product of TMPD and/or 2-ethylhexane-1,3-diol with 1 to 10 moles of ethylene oxide, and preferably with 1 to 5 moles of ethylene oxide, as well as analogs alkoxylated with other $C_3$ or $C_4$ alkyl oxides or mixtures of any of $C_2$, $C_3$ and/or $C_4$ alkyl oxides. Since the diol which is alkoxylated includes one primary hydroxyl group and one secondary hydroxyl group, the alkoxylation proceeds predominantly at the primary hydroxyl group.

The compositions which contain one or more compounds of formulas (I) and/or (II) can also contain one or a mixture of compounds of structural formula (E)

$$R^{E1}-C(O)O-R^{E2}-(OC(O)R^{E3})_{0-1} \quad (E)$$

wherein $R^{E1}$ is straight, cyclic or branched alkyl containing 1–15 carbon atoms, and $R^{E1}$ is substituted with 0 to 3 hydroxyl groups; and wherein $R^{E2}$ is straight, cyclic or branched alkyl containing 1 to 10 carbon atoms, and $R^{E2}$ is substituted with 0 to 3 hydroxyl groups, and $R^{E2}$ can optionally be substituted with a group of the structure —OC(O)—$R^{E3}$ wherein $R^{E3}$ is straight, cyclic or branched alkyl containing 1 to 15 carbon atoms and is optionally substituted with a hydroxyl group.

Preferred compounds of structural formula (E) include those wherein $R^{E2}$ contains 2 or 3 carbon atoms, for example, glycol and glyceryl derivative, or $R^{E2}$ contains about 8 carbon atoms, for example, derivatives of 2,2,4-trimethylpentanediol or of 2-ethylhexanediol. Preferred compounds of structural formula (E) include 2,2,4-trimethyl-1,3-pentanediol monoisobutyrate, hydroxypivalyl hydroxypivalate, and the monoester of TMPD with hydroxypivalic acid.

Formulations can also contain what may be termed aesthetic additives to provide properties such as fragrance, preservative, viscosity control, and color. Such additives are discussed below. The formulations according to the present invention generally exhibit highly satisfactory viscosities, generally as pourable and even sprayable fluids.

F. ADDITIONAL SURFACTANTS

Other suitable non-quaternary compound surfactants, whether anionic, cationic, zwitterionic, nonionic, or amphoteric, may be used in combination with the compounds and formulations of the invention, depending on the application.

1. General Surfactants

For example, in a fabric softening application, suitable anionic surfactants may include, without limitation, the alkylbenzene sulfonates, α-olefin sulfonates, and xylene sulfonates available from Witco Corporation under the WITCONATE® trademark. While these surfactants may be unsuitable for personal care applications because they may cause skin and eye irritation, surfactants suitable for personal care applications may be used in other non-personal care applications.

2. Personal Care Surfactants

For personal care applications, suitable anionic surfactants would include, without limitation, ammonium lauryl sulfate, sodium lauryl sulfate, any α-olefin sulfonate, ammonium laureth sulfate (2 or 3 moles), sodium laureth sulfate (2 or 3 moles), sodium myristyl sulfate, sodium myristeth sulfate (1–4 moles), ammonium xylene sulfonate, sodium xylene sulfonate, TEA dodecylbenzene sulfonate, TEA lauryl sulfate, ammonium pareth sulfate, sodium pareth sulfate, sodium oleth sulfate, derivatives of any of the forgoing, and similar compounds known to those of skill in the art, and mixtures thereof. For personal care applications, suitable amphoteric surfactants or non-ionic surfactants include betaines, sulfosuccinates, mono- and diglycerides, glycinates, sugars and derivatives thereof, hydroxysultaines, mono- and diacetates, ethoxylated derivatives of any of the forgoing, and similar compounds known to those of skill in the art, and mixtures thereof. Preferred surfactants include cocamidopropyl betaine, lauramidopropyl betaine, ricinoleamidopropyl betaine, myristamidopropyl betaine, palmamidopropyl betaine, stearamidopropyl betaine, behenamidopropyl betaine, erucamidopropyl betaine, cocamidopropyl hydroxysultaine, myristamidopropyl hydroxysultaine, palmamidopropyl hydroxysultaine, stearamidopropyl hydroxysultaine, behenamidopropyl hydroxysultaine, erucamidopropyl hydroxystultaine, disodium lauroamphodiacetate, disodium cocamphodiacetate, disodium myristamphodiacetate, disoditiuim palmamnplhodiacetate, disodium stearampphodiacetate, disodium beheniampliodiacetate, disodium erucamphodiacetate, sodium lauryl amphoacetate, sodium cocamphoacetate, sodium cocoamphopropionate, sodium laurylam phopropionate, disodium lauroamphodipropionate, sodium lauryl sulfosuccinate, disodium laureth sulfosuccinate, cocobetaine, laurylbetaine, myristylbetaine, stearylbetaine, behenylbetaine, PEG 1-300 glyceryl cocoate, PEG 1-300 glyceryl tallowate, PEG 1-500 hydrogenated glyceryl palmitate, coco-glucoside, lauryl glucoside, decyl glucoside, and mixtures thereof.

Other surfactants that may be added to these systems include, but are not limited to, alkanolamides such as almondamide diethanolamine (DEA), behenamide DEA, cocamide DEA, hydrogenated tallowamide DEA, isostearamide DEA, lactamide DEA, lauramide DEA, linoleamide DEA, myristamide DEA, oleamide DEA, palmamide DEA, palmitamide DEA, ricinoleamide DEA, soyamide DEA, stearamide DEA, tallamide DEA, and tallowamide DEA. Preferred alkanolamides include acetamide monoethanolamine (MEA), behenamide MEA, cocamide MEA, hydroxystearamide MEA, isostearamide MEA, lactamide MEA, lauramide MEA, linoleamide MEA, myristamide MEA, oleamide MEA, palmamide MEA, palmitamide MEA, ricinoleamide MEA, stearamide MEA, tallowamide MEA, undecylenamide MEA, cocamide monoisopropylamine (MIPA), hydroxyethyl stearamide MIPA, isostearamide MIPA, lauramide MIPA, linoleamide MIPA, myristamide MIPA, oleamide MIPA, palmamide MIPA, ricinoleamide MIPA, and stearamide MIPA. Some of these alkanolamides are available from Witco Corporation under the WITCAMIDE® tradename.

In addition, various amine oxides may be used in these systems. Preferred amine oxides include, but are not limited to, behenamine oxide, cocamidopropylamine oxide, cocamine oxide, decylamine oxide, dihydroxyethylcocamine oxide, dihydroxyethyllauramine oxide, dihydroxyethyltallowamine oxide, hydrogenated palm kernel amine oxide, hydrogenated tallowamine oxide, isostearamidopropylamine oxide, lauramidopropylamine oxide, lauramine oxide, myristamidopropylamine oxide, myristamine oxide, oleamidopropylamine oxide, oleamine oxide, palmitamidopropylamine oxide, palmitamine oxide, soyamidopropylamine oxide, stearamidopropylamine oxide, stearamine oxide, tallowamidopropylamine oxide, tallowamine oxide, and undecylenamidopropylamine oxide. Several of these materials are available from Witco Corporation under the VAROX® tradename.

G. PERSONAL CARE EMOLLIENTS AND EMULSIFIERS

Emollients and emulsifiers are also typically used in personal care formulations in combination with the polyester amine compounds and polyquatermlary compounds of the invention, depending on the application.

1. Personal Care Emollients

The preferred embodiment of this invention may also be used in emulsions that can be used as skin or hair conditioners which can take the form of lotions, creams, leave-on products, and rinse-off products. These systems may also include additional products that may improve the feel and conditioning, or the emolliency of skin and hair. In addition to some of the materials mentioned above that can also function as conditioning agents, preferred additives for this use include, but are not restricted to, acetylated lanolin, aminopropyl dimethicone, ammonium hydrolyzed collagen, ammonium lauroyl sarcosinate, amodimethicone, amodimethicone/dimethicone copolyol, amodimethicone hydroxystearate, capryloyl hydrolyzed collagen, cetyl alcohol, cetyl esters, cetyl laurate, cocamidopropyl dimethylamine dihydroxymethylpropionate, cocoyl hydrolyzed soy protein, collagen, disodium cocoamphodiacetate, disodium cocoamphodipropionate, dioctyl dimerate, ditridecyl adipate, glycerine, glyceryl oleate, glyceryl stearate, hydrogenated soybean oil, hydrogenated tallow glycerides, isocetyl stearate, jojoba (*Buxus chinensis*) oil, keratin, lanolin, milk protein, mineral oil, oat (*Avena sativa*) protein, octyl cocoate, oleyl myristate, oleyl stearate, palm alcohol, palm glycerides, panthenol, PEG-10, PEG-32, PEG-100, PEG-200, petrolatum, PPG-6-sorbeth-245, stearyl citrate, tridecyl stearate, urea, vegetable oil, and wheat amino acids. Some of these products are available from Witco Corporation under the KEMSTRENE®, WITCONOL™, STARFOL®, and KEMESTER® tradenames.

2. Personal Care Emulsifiers

Such emulsions usually include emulsifiers to form and preserve the emulsion. In addition to some of the materials previously mentioned that also act as emulsifiers, some preferred emulsifiers for this use include, but are not restricted to behenth-5, beheneth-10, beheneth-20, butylglicoside caprate, ceteareth-2, ceteareth-10, ceteareth-18, ceteth-10, ceteth-16, corn oil PEG-8 esters, $C_{9-11}$ pareth-3, $C_{11-15}$ pareth-5, $C_{11-15}$ pareth-12, $C_{12-13}$ pareth-2, $C_{12-13}$ pareth-10, $C_{12-13}$ pareth-15, deceth-4, deceth-5, deceth-6, di-$C_{12-13}$ pareth-6 phosphate, di-$C_{12-15}$ pareth-8 phosphate, glyceryl cocoate, glyceryl laurate, glyceryl oleate, isoceteth-10, isodeceth-6, isosteareth-10, laureth-4, laureth-5, laureth-10, octyldodeceth-10, octyidodeceth-20, oleoyl ethyl glucoside, oleth-2, oleth-4, PEG-8 caprate, PEG-8 castor oil, PEG-7 cocamide, PEG-11 cocamide, PEG-15 cocoate, PEG-20 dilaurate, PEG-32 dilaurate, PEG-8 dioleate, PEG-2 distearate, PEG-8 distearate, PEG-8 glyceryl laurate, PEG-15 glyceryl laurate, PEG-4 isostearate, PEG-4 laurate, PEG-5 octanoate, PEG-9 oleamide, PEG-5 oleate, PEG-20 palmitate, PEG-6 stearate, PEG-16 tallate, polysorbate 20, polysorbate 80, steareth-10, trideceth-5, and undeceth-9.

H. OTHER ADDITIVES

Other additives and adjuvants can be optionally added to the compounds and formulations of the present invention for their known purposes. Such additives and adjuvants include, but are not limited to, perfumes, preservatives including-bacteriocides and fungicides, insect and moth repelling agents, polymeric soil release agents, antistatic agents, dyes and colorants, especially bluing agents, viscosity control agents, antioxidants, silicones, defoaming agents, antifoaming agents, emulsifiers, brighteners, opacifiers, freeze-thaw control agents, shrinkage control agents, aloe, humectants, skin protectants, feel modifiers, waxes, glycerine, vitamins and extracts, and mixtures thereof. The identity and amounts of the additives and adjuvants used would depend on the application of the formulation and its desired properties. The additives and adjuvants are well-known to those of skill in the art and the additives and adjuvants listed below are not meant to be an exhaustive list but merely a guide to the types of additives that would typically be used.

1. Perfumes

As noted above, perfumes or fragrance materials may be added to the compositions and formulations of the present invention. The selection of the perfume or perfumes is based upon the application, the desired effect on the consumer, and preferences of the formulator. The perfume selected for use in the compositions and formulations of the present invention contains ingredients with odor characteristics which are preferred in order to provide a fresh impression on the surface to which the composition is directed, for example, those which provide a fresh impression for fabrics if a fabric softener treatment formulation is prepared. Such perfume is preferably present at a level of from about 0.01% to about 5%, preferably from about 0.05% to about 3%, more preferably from about 0.1% to about 2%, by weight of the total composition.

Preferably, the perfume is composed of fragrance materials selected from the group consisting of aromatic and aliphatic esters having molecular weights from about 130 to about 250; aliphatic and aromatic alcohols having molecular weights from about 90 to about 240; aliphatic ketones having molecular weights from about 150 to about 260; aromaticketones having molecular weights from about 150 to about 270; aromatic and aliphaticlactones having molecular weights from about 130 to about 290; aliphaticaldehydes having molecular weights from about 140 to about 200; aromatic aldehydes having molecular weights from about 90 to about 230; aliphatic and aromatic ethers having molecular weights from about 150 to about 270; and condensation products of aldehydes and amines having molecular weights from about 180 to about 320; and mixtures thereof. The selection of such perfumes and fragrance materials are well-known to those of skill in the art, both for desired scent and appropriate scent impact. For example, when high initial perfume odor impact on fabrics is desired, it is preferable to select a perfume containing perfume ingredients which are not too hydrophobic. The degree of hydrophobicity of a perfume ingredient can be correlated with its octanol/water partitioning coefficient P, the ratio between its equilibrium concentration in octanol and in water. Thus, a perfume ingredient with a greater partitioning coefficient P is more hydrophobic and a perfume ingredient with a smaller partitioning coefficient P is more hydrophilic; a selection based on the application and intended effect may be made accordingly. For example, in a fabric application, the preferred perfume ingredients would have an octanol/water partitioning coefficient P of about 1,000 or smaller.

2. Preservatives

Optionally, solubilized, water-soluble preservatives can be added to the present invention. Preservatives are especially preferred when organic compounds that are subject to microorganisms are added to the compositions of the present invention, especially when they are used in aqueous compositions. When such compounds are present, long term and even short term storage stability of the compositions and formulations becomes an important issue since contamination by certain microorganisms with subsequent microbial growth often results in an unsightly and/or malodorous solution. Therefore, because microbial growth in these compositions and formulations is highly objectionable when it occurs, it is preferable to include a solubilized water-soluble, antimicrobial preservative, which is effective for inhibiting and/or regulating microbial growth in order to increase storage stability of the preferably clear and often aqueous compositions and formulations of the present invention.

Typical microorganisms that can be found personal care products include bacteria, for example, *Bacillus thuringiensis* (cereus group) and *Bacillus sphaericus*, and fungi, for example, *Aspergillus ustus*. *Bacillus sphaericus* is one of the most numerous members of Bacillus species in soils. In addition, microorganisms such as *Escherichia coli* and *Pseudomonas aerupinosa* are found in some water sources, and can be introduced during the preparation of aqueous solutions of the present invention.

It is preferable to use a broad spectrum preservative, for example, one that is effective on both bacteria (both gram positive and gram negative) and fungi. A limited spectrum preservative, for example, one that is only effective on a single group of microorganisms, for example, fungi, can be used in combination with a broad spectrum preservative or other limited spectrum preservatives with complimentary and/or supplementary activity. A mixture of broad spectrum preservatives can also be used.

Antimicrobial preservatives useful in the present invention can be biocidal compounds, that is, substances that kill microorganisms, or biostatic compounds, that is, substances that inhibit and/or regulate the growth of microorganisms. Preferred antimicrobial preservatives are those that are water-soluble and are effective at low levels. In general, the water-soluble preservatives that may be used include organic sulfur compounds, halogenated compounds, cyclic organic nitrogen compounds, low molecular weight aldehydes, quaternary compounds, dehydroacetic acid, phenyl and plienoxy compounds, and mixtures thereof. Examples of preservatives useful in the present invention include, but are not limited to, the short chain alkyl esters of p-hydroxybenzoic acid (commonly known as parabens); N-(4-chlorophenyl)-N-(3,4-dichlorophenyl)urea (also known as 3,4,4'-trichlorocarbanilide or triclocarban); 2,4,4'-trichloro-2'-hydroxydiphenyl ether, commonly known as triclosan); a mixture of about 77% 5-chloro-2-methyl-4-isothiazolin-3-one and about 23% 2-methyl-4-isothiazolin-3-one, a broad spectrum preservative available from the Rohm and Haas Company as a 1.5% aqueous solution under the tradename KATHON® CG; 5-bromo-5-nitro-1,3-dioxane, available from Henkel Corporation under the tradename BRONIDOX® L; 2-bromo-2-nitropropane-1,3-diol, available from Inolex Chemical Company under the tradename BRONOPOL™; 1,1'-hexamethylenebis(5-(p-chlorophenyl)biguanide) (commonly known as chlorhexidine) and its salts, for example, with acetic and digluconic acids; a 95:5 mixture of 1,3-bis(hydroxymethyl)-5,5-dimethyl-2,4-imidazolidinedione and 3-butyl-2-iodopropynyl carbamate, available from Lonza Inc. under the tradename GLYDANT® Plus; N-[-1,3-bis(hydroxymethyl)2,5-dioxo-4-imidazolidinyl]-N,N'-bis(hydroxy-methyl)urea, commonly known as diazolidinyl urea, available from Sutton Laboratories, Inc. under the tradename GERMALL® II; N,N"-methylenebis[N-[1-(hydroxymethyl)-2,5-dioxo-4-imidazolidinyl]urea] (commonly known as imidazolidinyl urea), available, for example, from 3V-Sigma under the tradename ABIOL™, from Induchem under the tradename UNICIDE® U-13, and from Sutton Laboratories, Inc. under the tradename GERMALL® 115; polymethoxy bicyclic oxazolidine, available from Hiils America Inc. under the tradename NUOSEPT®; formaldehyde; glutaraldehyde; polyaminopropyl biguanide, available from ICI Americas, Inc. under the tradename COSMOCIL® CQ or from Brooks Industries Inc. under the tradename MIKROKILL™; dehydroacetic acid; and mixtures thereof. In general, however, the preservative can be any organic preservative material which is appropriate for the application, for example, in a fabric softening application such preservative will preferably not cause damage to fabric appearance, for example, discoloration, coloration, or bleaching of the fabric.

If the antimicrobial preservative is included in the compositions and formulations of the present invention, it is preferably present in an effective amount, wherein an "effective amount" means a level sufficient to prevent spoilage or prevent growth of inadvertently added microorganisms for a specific period of time. Preferred levels of preservative are from about 0.0001% to about 0.5%, more preferably from about 0.0002% to about 0.2%, most preferably from about 0.0003% to about 0.1%, by weight of the composition.

Bacteriostatic effects can sometimes be obtained for aqueous compositions by adjusting the composition pH to an acid pH, for example, less than about pH 4, preferably less than about pH 3. Low pH for microbial control is not a preferred approach in the present invention because the low pH can cause chemical degradation of the cyclodextrins. Therefore, aqueous compositions of the present invention should have a pH greater than about 3.0, preferably greater than about 4.0, more preferably greater than about 4.5. As stated above, it is preferable to use the preservative at an effective amount, as defined hereinabove. Optionally, however, the preservative can be used at a level which provides an antimicrobial effect on the treated fabrics.

3. Antistatic Agents

The composition of the present invention can optionally contain an effective amount of antistatic agent to provide the treated clothes with in-wear static. Preferred antistatic agents are those that are water soluble in at least effective amount, such that the composition remains a clear solution. Examples of these antistatic agents include monoalkyl cationic quaternary ammonium compounds, for example, mono ($C_{10}$–$C_{14}$ alkyl)trimethyl ammonium halide, such as monolauryl trimethyl ammonium chloride, hydroxycetyl iiydroxyethlyl dimethyl ammonium chloride (available from Henkel Corporation under the tradename DEHYQUART® E), and ethyl bis(polyethoxyethanol) alkylammonium etllylsulfate (available from Witco Corporation under the tradename VARIQUAT® 66), polyethylene glycols, polymeric quaternary ammonium salts (such as those available from Rhône-Poulenc Corporation under the MIRAPOL® tradename), quaternized polyethyleneimines, vinylpyrrolidone/methacrylamidopropyltrimethylammonium chloride copolymer (available from GAF Corporation under the tradename GAFQUAT® HS-100), triethonium hydrolyzed collagen ethosulfate (available from Maybrook Inc. under the tradename QUAT-PRO™ E), and mixtures thereof.

It is preferred that a no foaming, or low foaming, agent is used, to avoid foam formation during fabric treatment. It is also preferred that polyethoxylated agents such as polyethylene glycol or VARIQUAT® 66 are not used when α-cyclodextrin is used. When an antistatic agent is used it is typically present at a level of from about 0.05% to about 10%, preferably from about 0.1% to about 5%, more preferably from about 0.3% to about 3%, by weight of the composition.

4. Dyes and Colorants

Colorants and dyes, especially bluing agents, can be optionally added to the compositions of the present invention for visual appeal and performance impression. When colorants are used, they are used at extremely low levels to avoid fabric staining. Preferred colorants for use in the present compositions are highly water-soluble dyes, for example, LIQUITINT® dyes available from Milliken Chemical Company. Non-limiting examples of suitable dyes are, LIQUITINT® Blue HP, LIQUITINT® Blue 65, LIQUITINT® Patent Blue, LIQUITINT® Royal Blue, LIQUITINT® Experimental Yellow 8949-43, LIQUITINT® Green HMC, LIQUITINT® Yellow II, and mixtures thereof. Any dye can be used in the compositions of the present invention, but nonionic dyes are preferred to decrease interaction with dye transfer inhibitor. Useful acid dyes include: Polar Brilliant Blue, and D&C Yellow #10, both supplied by Hilton Davis Chemical Company. Nonionic LIQUITINT® dyes supplied by Milliken Chemical Company are also useful.

For many personal care products using the present invention, colorants are also added at extremely low levels. Color additives for products to be marketed in the United States are named in compliance with Title 21 of the U.S. Code of Federal Regulations. Suitable colors include, but are not limited to, Acid Black 1, Acid Blue 3, Acid Blue 9 Aluminum Lake, Acid Blue 74, Acid Green 1, Acid Orange 6, Acid Red 14 Aluminum Lake, Acid Red 27, Acid Red 27 Aluminum Lake, Acid Red 51, Acid Violet 9, Acid Yellow 3, Acid Yellow 3 Aluminum Lake, Acid Yellow 73, Aluminum Powder, Basic Blue 6, Basic Yellow β-Carotene, Brilliant Black 1, Bromocresol Green, Chromium Oxide Greens, CI 12010, CI 12120, CI 28440, CI 71105, Curry Red, D&C Blue No. 1 Aluminum Lake, D&C Blue No. 4, D&C Brown No. 1, D&C Green No. 3 Aluminum Lake, D&C Green No. 5, D&C Orange No. 4 Aluminum Lake, D&C Red No. 6, D&C Red No. 6 Aluminum Lake, D&C Violet No. 2, D&C Yellow No. 7, D&C Yellow No. 11, D&C Blue No. 1, FD&C Yellow No. 5 Aluminium Lake, iron oxides, Pigment Orange 5, Pigment Red 83, Pigment Yellow 73, Solvent Orange 1, Solvent Yellow 18, ultramarines, and zinc stearate.

5. Insect and Moth Repelling Agents

The composition of the present invention can optionally contain an effective amount of insect or moth repelling agents. Typical insect and moth repelling agents are pheromones, such as anti-aggregation pheromones, and other natural and/or synthetic ingredients. Preferred insect and moth repellent agents useful in the composition of the present invention are perfume ingredients, such as citronellol, citranellal, citral, linalool, cedar extract, geranium oil, sandalwood oil, 2-(diethylphenoxy)ethanol, 1-dodecene, and the like. Other examples of insect and/or moth repellents useful in the composition of the present invention are disclosed in U.S. Pat. Nos. 4,449,987; 4,693,890; 4,696,676; 4,933,371; 5,030,660; and 5,196,200; and in B. D. Mookherjee et al., "Semio Activity of Flavor and Fragrance Molecules on Various Insect Species", published in *Bioactive Volatile Compounds from Plants*, ASC Symposium Series 525, R. Teranishi, R. G. Buttery, and H. Sugisawa (eds.), 1993, pp. 35–48. All of these patents and publications are herein incorporated by reference in their entireties. When an insect and/or moth repellent is used it is typically present at a level of from about 0.005 wt. % to about 3 wt. % of the composition.

6. Polymeric Soil Release Agents

Soil release agents, usually polymers, are especially desirable additives at levels of from about 0.05 wt. % to about 5 wt. %, preferably from about 0.1 wt. % to about 4 wt. %, more preferably from about 0.2 wt. % to about 3 wt. %. Suitable soil release agents are disclosed in U.S. Pat. Nos. 4,702,857; 4,711,730; 4,713,194; 4,877,896; 4,956,447; and 4,749,596, all of these patents being herein incorporated by reference in their entireties.

Especially desirable optional ingredients are polymeric soil release agents comprising block copolymers of polyalkylene terephthalate and polyoxyethylene terephthalate, and block copolymers of polyalkylene terephthalate and polyethylene glycol. The polyalkylene terephthalate blocks preferably comprise ethylene and/or propylene groups. Many such soil release polymers are nonionic, for example, the nonionic soil release polymer is described in U.S. Pat. No. 4,849,257, which patent is herein incorporated by reference in its entirety.

The polymeric soil release agents useful in the present invention can include anionic and cationic polymeric soil release agents. Suitable anionic polymeric or oligomeric soil release agents are disclosed in U.S. Pat. No. 4,018,569, which patent is herein incorporated by reference in its entirety. Other suitable polymers are disclosed in U.S. Pat. No. 4,808,086, which patent is herein incorporated by reference in its entirety. Suitable cationic soil release polymers are described in U.S. Pat. No. 4,956,447, which patent has already been herein incorporated by reference.

7. Viscosity Control Agents

Viscosity control agents can be organic or inorganic in nature and may either lower or raise the viscosity of the formulation. Examples of organic viscosity modifiers (lowering) are aryl carboxylates and sulfonates (for example, benzoate, 2-hydroxybenzoate, 2-aminobenzoate, benzenesulfonate, 2-hydroxybenzenesulfonate, 2-aminobenzenesulfonate, etc.), fatty acids and esters, fatty alcohols, and water-miscible solvents such as short chain alcohols. Examples of inorganic viscosity control agents are water-soluble ionizable salts. A wide variety of ionizable salts can be used. Examples of suitable salts are the halides and acetates of ammonium ion and the group IA and IIA metals of the Periodic Table of the Elements, for example, calcium chloride, lithium chloride, sodium chloride, potassium chloride, magnesium chloride, ammonium chloride, sodium bromide, potassium bromide, calcium bromide, magnesium bromide, ammonium bromide, sodium iodide, potassium iodide, calcium iodide, magnesium iodide, ammonium iodide, sodium acetate, potassium acetate, or mixtures thereof. Calcium chloride is preferred. The ionizable salts are particularly useful during the process of mixing the ingredients to make the compositions herein, and later to obtain the desired viscosity. The amount of ionizable salts used depends on the amount of active ingredients used in the compositions and can be adjusted according to the desire of the formulator. Typical levels of salts used to control the composition viscosity are from 0 to about 10 wt. %, preferably from about 0.01 wt. % to about 6 wt. %, and most preferably from about 0.02 wt. % to about 3 wt. % of the composition.

Viscosity modifiers (raising) or thickening agents can be added to increase the ability of the compositions to stably suspend water-insoluble articles, for example, perfume microcapsules. Such materials include hydroxypropyl substituted guar gum (such as that available from Rhône- Poulenc Corporation under the tradename JAGUAR® HP200), polyethylene glycol (such as that available from Union Carbide Corporation under the tradename CARBOWAX® 20M), hydrophobic modified hydroxyethylcellulose (such as that available from the Aqualon Company under the tradename NATROSOL® Plus), and/or organophilic clays (for example, hectorite and/or bentonite clays such as those available from the Rheox Company under the tradename BENTONE™ 27, 34 and 38 or from Southern Clay Products under the tradename BENTOLITE™ L; and those described in U.S. Pat. No. 4,103,047, which is herein incorporated by reference in its entirety). These viscosity raisers (thickeners) are typically used at levels from about 0.5 wt. % to about 30 wt. %, preferably from about 1 wt. % to about 5 wt. %, more preferably from about 1.5 wt. % to about 3.5 wt. %, and most preferably from about 2 wt. % to about 3 wt. %, of the composition.

8. Pearlizing and Opacifying Agents

Examples of pearlizing or opacifying agents that can be added to the compositions of this invention include, but are not restricted to, glycol distearate, propylene glycol distearate, and glycol stearate. Some of these products are available from Witco Corporation under the KEMESTER® tradename.

9. Vitamins and Extracts

In personal care applications, vitamins and extracts are often used in the formulations thereof. Examples of vitamins that can be added to the compositions of this invention include, but are not restricted to, vitamins $A_1$, $A_2$, $B_1$, $B_2$, $B_6$, $B_{12}$, C, D, E, H, and K, the provitamins, salts, derivatives, and complexes thereof, and mixtures thereof. Examples of extracts that can be added to the compositions of this invention include, but are not restricted to, rosemary extract, carrot extract, *Camelina sativa*, camomile extract, egg yolk extract, elm extract, acacia extract, rose extract, lilac extract, licorice extract, lemon extract, orange extract, lime extract, linden extract, melon extract, peach extract, orchid extract, orris extract, and the like, and mixtures thereof.

10. Antioxidants

Examples of antioxidants that can be added to the compositions of this invention are propyl gallate, available from Eastman Chemical Products, Inc. under the tradenames TENOX® PG and TENOX® S-1, and dibutylated hydroxytoluene, available from UOP Inc. under the tradename SUSTANE® BHT.

11. Silicones

The present compositions can contain silicones to provide additional benefits, for example, in a fabric application they may provide ease of ironing and improved fabric absorbency. As used herein, the term "silicones" comprises cationic and amplioteric silicones, polysiloxanes, and polysiloxanes having hydrogen-bonding functional groups consisting of amino, carboxyl, hydroxyl, ether, polyether, aldehyde, ketone, amide, ester, and thiol groups. Such polysiloxanes include, but are not limited to, polyether-modified polysiloxanes, amino-modified polysiloxanes, epoxy-modified polysiloxanes, polyhydrido-modified polysiloxanes, phenol-derivative-modified polysiloxanes, ABA-type polysiloxanes, $[AB]_N$-type polysiloxanes, amino $[AB]_N$-type polysiloxanes, including those available from OSi Specialties, Inc. (a division of Witco Corporation), under the SILWET®, NUWET®, NUDRY™, NUSOFT™, MAGNASOFT® tradenames.

Suitable silicones may include polydimethylsiloxanes of viscosity of from about 100 centistokes (cs) to about 100,000 cs, preferably from about 200 cs to about 60,000 cs and/or silicone gums. These silicones can be used in emulsified form, which can be conveniently obtained directly from the suppliers. Examples of these preemulsified silicones are the 60% emulsion of polydimethylsiloxane (350 cs) sold by Dow Corning Corporation under the tradename DOW CORNING® 1157 Fluid and the 50% emulsion of polydimethylsiloxane (10,000 cs) sold by General Electric Company under the tradename GENERAL ELECTRIC® SM 2140 silicones. The optional silicone component can be used in an amount of from about 0.1 wt. % to about 6 wt. % of the composition.

Silicone foam suppressants can also be used. These are usually not emulsified and typically have viscosities of from about 100 cs to about 10,000 cs, preferably from about 200 cs to about 5,000 cs. Very low levels are used, typically from about 0.01% to about 1%, preferably from about 0.02% to about 0.5%. Another preferred foam suppressant is a silicone/silicate mixture, for example, Dow Corning's ANTIFOAM™ A.

The pH (10% solution) of the compositions of this invention is generally adjusted to be in the range of from about 2 to about 7, preferably from about 2.4 to about 6.5, more preferably from about 2.6 to about 4. Adjustment of pH is normally carried out by including a small quantity of free acid in the formulation. Because no strong pH buffers are present, only small amounts of acid are required. Any acidic material can be used; its selection can be made by anyone skilled in the softener arts on the basis of cost, availability, safety, etc. Among the acids that can be used are methyl sulfonic, hydrochloric, sulfuric, phosphoric, citric, maleic, and succinic. For the purposes of this invention, pH is measured by a glass electrode in a 10% solution in water of the softening composition in comparison with a standard calomel reference electrode.

12. Lubrication and Slip Additives

Compositions and formulations of the present invention can contain additives such as water, insoluble organics such as fatty acids, fatty esters, triglycerides, oils, alcohols, fatty alcohols, fatty amines and derivatives, amides, hydrocarbons, mineral oils, waxes, and the like, and mixtures thereof, as lubrication and slip agents.

13. Dye Transfer Inhibitors

Compositions and formulations of the present invention can contain ethoxylated amines, amphoterics, betaines, polymers such as polyvinylpyrrolidone, and other ingredients that inhibit dye transfer.

I. EXAMPLES

The above examples are but a few examples of more particular formulations embodying the compositions of the present invention. The following examples are provided for purposes of further description of the present invention and are not intended to limit the scope of that which is regarded as the invention.

Testing of WE-18 and V3626 Under U.S. Conditions

A Pairwise Ranking method was used for this testing, which is different from our normal method of Forced Ranking. The method is described by Meilgaard, Civille, and Carr, *Sensory Evaluation Techniques*, (pp. 88–91, 254, and 268) and is being looked at by a CSMA committee. Hard tallow solketal esterquat (SEQ) softens as well as HEQ while the soft tallow an canola were worse.

Example 1 is softening testing done for Lever's Kuschelweich (HEQ), "improved" WE-18 (lot GS58101) and V3626 (lot GS58141). The method is explained as follows: 15% dispersions were made of WE-18 and V3626 (pH=3, about 850 ppm calcium chloride (100% bases) added for viscosity control. Solids on Kuschelweich 15.2%; the standard AATCC detergent was used in the wash cycle; 0.1% loading of softener was used on the bundle weight; and all towels dried in a electric dryer.

Three Towel Study <<<Paired Set>>>

| WE-18 towel 1 | V3626 towel 1 | WE-18 towel 3 | V3626 towel 4 |
| WE-18 towel 2 | HEQ towel 3 | WE-18 towel 4 | HEQ towel 1 |
| V3626 towel 2 | HEQ towel 2 | V3626 towel 3 | HEQ towel 4 |

Analysis Results

Table 1 shows the number of times (out of 10) each "column" sample was chosen as being softer than each "row" sample. For example, when towel WE-18 was presented with towel HEQ, it (WE-18) was perceived softer 9 out of the 10 times.

TABLE 1

Comparison of towel samples

| | WE-18 | V3626 | HEQ |
|---|---|---|---|
| WE-18 | — | 2 | 1 |
| V3626 | 8 | — | 0 |
| HEQ | 9 | 10 | — |

The first step in the Friedman analysis is to compute the rank sum for each sample as follows:

WE-28: 2(8+9)+(2+1)=37

V3626: 2(2+10)+(8+0)=48

HEQ: 2(1+0)+(9+10)=21

The Honestly significant difference at 95% (HSD95) is a standard statistical measure calculated as follows: HSD95= $q^{0.05}(pt/4)^{1/2}$, where $q^{0.05}$ is a constant for a particular number of samples (3.31 for 3 samples); p is the number of judgments (10 for this test); t is the number of treatments of samples tested (3 for this test). For this evaluation, HSD95 was calculated as 9.06. Taking the difference between the rank sums of V3626, WE-18, and HEQ, the differences are greater than 9.06. Consequently, V3626 and WE-18 are "significantly" softer than HEQ.

Softening testing was done on WE-18, V3626 and Kuschelweich (HEQ). The following points need to be outlined concerning this test: softening evaluations were done on both line dried and dryer dried towels; no detergent was used in the wash cycle; sample WE-18 (lot GS59078) upon dispersing in water resulted in a high viscosity (over 5000 cP) formulation; and a high loading of softener was added to the bundle weight (0.28%)

TABLE 2

Line Dry Softening Results

| | WE-18 | V3626 | HEQ |
|---|---|---|---|
| WE-18 | — | 13 | 11 |
| V3626 | 1 | — | 8 |
| HEQ | 3 | 6 | — |

Ranked sums: HEQ = 47 WE-18 = 32 V3636 = 47 HSD95 for this test 10.7
Results: HEQ is softer than WE-18. There is no difference in softening between V3626 and HEQ.

Ranked Sums

HEQ=47

WE-18=32

V3626=47

HSD95 for this test 10.7

Results

HEQ is softer than WE-18. There is no difference in softening between V3626 and HEQ.

TABLE 3

Dryer Dry Softening Results

| | WE-18 | V3626 | HEQ |
|---|---|---|---|
| WE-18 | — | 1 | 5 |
| V3626 | 13 | — | 11 |
| HEQ | 9 | 3 | — |

Ranked sums: HEQ = 50 WE-18 = 32 V3636 = 44 HSD95 for this test 10.7
Results: HEQ is softer than WE-18. There is no difference in softening between V3626 and HEQ.

Solketal Derivative Softening Results Under U.S. Conditions

Several derivatives of solketal ester quats were tested for towel softening vs. Kuschelweich (HEQ) and WE-16. The solketal derivatives were canola-based, soft tallow-based, and hard tallow-based. These were compared using the normal Forced Ranking method. The following charts summarizes the softening results done on these solketal quat esters.

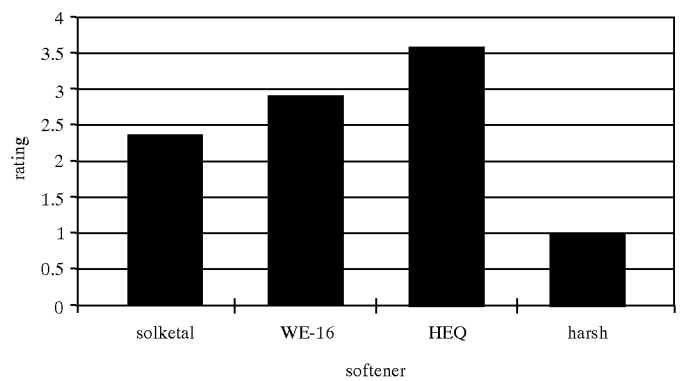

Chart 1: Soft tallow solketal

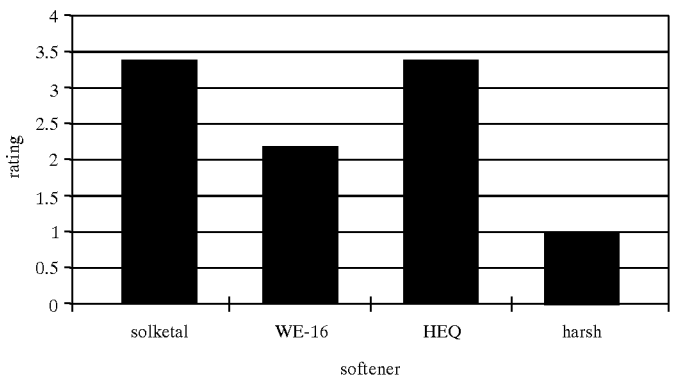

Chart 2
hardtallow solketal ester quat

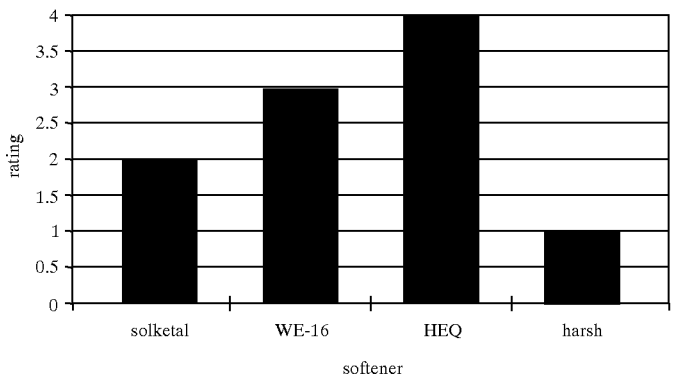

Chart 3
canola solketal ester quat

There are many unexpected benefits of the above formulations. Most importantly, there is improved softening performance of the formulation over an equivalent amount of dialkyl ester quat formulation absent compounds of formulas (I) and/or (II). In addition, however, the formulations above disperse readily into water, even cold water, without a viscosity increase as with conventional quats, and provide a finer final particle size when so dispersed, for example, at 100 ppm concentration.

EXAMPLE 1: Fabric Softener

| Component | Amount (weight %) |
|---|---|
| Component A | 20.8 |
| Dye (1% solution of SANDOLAN ® Walkblau NBL 150, available from Sandoz) | 0.60 |
| Antifoam (SAG 220, available from OSi Specialties) | 0.20 |
| Fragrance ® perfume oil (D 60515 W, available from Haarmann and Reimer GmbH) | 0.80 |
| Calcium chloride | 0.10 |
| Water, 9° German hardness | to 100 |

EXAMPLE 2: Fabric Softener

| Component | Amount (weight %) |
|---|---|
| Component B | 22.0 |
| Dye (1% solution of SANDOLAN ® Walkblau NBL 150, available from Sandoz) | 0.60 |
| Antifoam (SAG 220, available from OSi Specialties) | 0.20 |
| Fragrance ® perfume oil (D 60515 W, available from Haarmann and Reimer GmbH) | 0.80 |
| Calcium chloride | 0.10 |
| Water, 9° German hardness | to 100 |

EXAMPLE 3: Fabric Softener

| Component | Amount (weight %) |
|---|---|
| Component C | 20.5 |
| Dye (1% solution of SANDOLAN ® Walkblau NBL 150, available from Sandoz) | 0.60 |
| Antifoam (SAG 220, available from OSi Specialties) | 0.20 |
| Fragrance ® perfume oil (D 60515 W, available from Haarmann and Reimer GmbH) | 0.80 |

EXAMPLE 3: Fabric Softener

| Component | Amount (weight %) |
| --- | --- |
| Calcium chloride | 0.10 |
| Water, 9° German hardness | to 100 |

EXAMPLE 4: Fabric Softener

| Component | Amount (weight %) |
| --- | --- |
| Component D | 21.6 |
| Dye (1% solution of SANDOLAN ® Walkblau NBL 150, available from Sandoz) | 0.60 |
| Antifoam (SAG 220, available from OSi Specialties) | 0.20 |
| Fragrance ® perfume oil (D 60515 W, available from Haarmann and Reimer GmbH) | 0.80 |
| Calcium chloride | 0.10 |
| Water, 9° German hardness | to 100 |

EXAMPLE 5: Fabric Softener

| Component | Amount (weight %) |
| --- | --- |
| Component F | 20.5 |
| Dye (1% solution of SANDOLAN ® Walkblau NBL 150, available from Sandoz) | 0.60 |
| Antifoam (SAG 220, available from OSi Specialties) | 0.20 |
| Fragrance ® perfume oil (D 60515 W, available from Haarmann and Reimer GmbH) | 0.80 |
| Calcium chloride | 0.10 |
| Water, 9° German hardness | to 100 |

EXAMPLE 6: Fabric Softener

| Component | Amount (weight %) |
| --- | --- |
| Component F | 21.6 |
| Dye (1% solution of SANDOLAN ® Walkblau NBL 150, available from Sandoz) | 0.60 |
| Antifoam (SAG 220, available from OSi Specialties) | 0.20 |
| Fragrance ® perfume oil (D 60515 W, available from Haarmann and Reimer GmbH) | 0.80 |
| Calcium chloride | 0.10 |
| Water, 9° German hardness | to 100 |

EXAMPLE 7: Hair Rinse

| Component | Amount (weight %) |
| --- | --- |
| Component C | 2.3 |
| Propoxylated myristyl alcohol (INCI name: PPG-3 myristyl ether) (available from Witco A.Z., France under the tradename WITCONOL ® A PM) | 1.0 |
| Glyceryl stearate SE (available from Goldschmidt under the tradename TEGENACID ®) | 1.0 |
| Hydroxyethylcellulose (available from Aqualon under the tradename NATROSOL ® HHG) | 1.0 |
| Citric acid | 0.05 |
| Deionized water | to 100 |

Example 7 shows improved wet and dry combability of washed hair.

EXAMPLE 8: Car Rinse

| Component | Amount (weight %) |
| --- | --- |
| Component G | 8.8 |
| PEG-30 glyceryl cocoate (available from Witco Surfactants GmbH under the tradename REWODERM ® LI 63) | 7.3 |
| 2-ethylhexyl stearate (available from Henkel KGaA under the tradename RILONIT ® EHS) | 7.0 |
| Methyl ester of a fatty acid having 8–18 carbon atoms | 4.0 |
| Oleic acid imidazoline ether sulfate (available from Witco GmbH under the tradename REWOQUAT ® W 3690) | 7.3 |
| Dipropylene glycol mono-n-butyl ether (available from Dow Chemicals under the tradename DOWANOL ® DPnB) | 20.0 |
| Butylidiglycol | 10.0 |
| Deionized water | to 100 |

Example 8 shows improved water bead-off behavior on the surfaces of car bodies.

EXAMPLE 9: Car Shampoo

| Component | Amount (weight %) |
| --- | --- |
| Component G | 20.0 |
| Dipropylene glycol | 15.0 |
| Ethoxylated lauryl alcohol (available from Witco Surfactants GmbH under the tradename REWOPAL ® LA 12-80) | 28.0 |
| Cocoamidopropyl N-oxide (available from Witco Surfactants GmbH under the tradename REWOMINOX ® B 204) | 10.0 |
| Citric acid | 0.9 |
| Trisodium salt of methylglycinediacetic acid (available from BASF under the tradename Trilon ® M) | 2.0 |
| Deionized water | to 100 |

Example 9 shows improved cleaning action with increased gloss of the surface cleaned.

EXAMPLE 10: Hydrophilic Handle Modifier

| Component | Amount (weight %) |
| --- | --- |
| Component D | 65.0 |
| Coconut fatty acid polyglycol ester 8 EO (available from Witco Corp. under the tradename WITCONOL ® 2650) | 20.0 |
| Ethoxylated coconut fatty acid partial glycerides (available from Witco Surfactants GmbH under the tradename REWODERM ® ES 90/REWODERM ® LI 63 in the ratio 1:1) | 10.0 |
| Lauryl ether citrate (available from Witco Corp. under the tradename (WITCONOL ® EC 1127) | 5.0 |

This 100% strength formulation can be diluted with water as desired and adjusted to the desired viscosity. The handle and the rewetting power of the formulation in Example 10 were superior to those for a formulation in which Component D was replaced by a conventional esterquat (REWOQUAT® WE 18).

EXAMPLE 11: Permanent Hydrophilization Composition

| Component | Amount (weight %) |
|---|---|
| Component G | 50.0 |
| Coconut fatty acid polyglycol ester 8 EO (available from Witco Corp. under the tradename WITCONOL ® 2650) | 30.0 |
| Magnasoft Plus Fluid (Witco Corporation) | 10.0 |
| Magnasoft TLC (Witco Corporation) | 5.0 |
| Lauryl ether citrate (available from Witco Corp. under the tradename (WITCONOL ® EC 1127) | 5.0 |

This 100% strength formulation can be diluted with water as desired and adjusted to the desired viscosity. The handle and rewetting power of the formulation in Example 11 were superior to those for a formulation in which Component G was replaced by a conventional esterquat (REWOQUAT® WE 18).

Example A

This example illustrates formulations of compounds according to the present invention that are formulated into a microemulsion. As noted above, such formulations generally include three components: (a) a compound of formulas (I) and/or (II), (b) a solvatrope or coupling agent and blends thereof, and (c) an oil or hydrophobic organic component and blends thereof, which are blended in water.

Suitable solvatropes or coupling agents may be selected from the diols and alkoxylates corresponding to structural formulas (T) or (E), TMPD, TMPD alkoxylates, ethanol, isopropanol, butanol, 1,2-cyclohexanedimethanol (1,2-CHDM), 1,4-cyclohexanedimethanol (1,4-CHDM), HPHP glycol, isopentyidiol, 1,2-hexanediol, ethylene glycol butyl ether, hexylene glycol, 2-butoxyethanol (sold by Union Carbide under the tradename butyl CELLOSOLVE®), $C_6$–$C_{12}$ diols/triols and ester diols/triols, glycol ethers, and the like. Oils and hydrophobic organic components may be selected from the fatty $C_8$–$C_{22}$ methyl esters, such as methyl oleate, mineral seal oils, silicone oils, fatty acids, monoglycerides, diglycerides, triglycerides, dialkyl esters, and the like, depending on the application. The methyl esters are the preferred oil based on performance and biodegradability, although mineral seal oil is preferred in car drying aid applications.

Example B

This example illustrates formulations of compounds according formulas (I) and/or (II) for use as emulsifiers, for example, for agricultural emulsifiers or asphalt emulsifiers. Thus, these compounds are useful as an emulsifier for organic compounds, for example, when formulated with pesticides, other surfactants and dispersants, and water, the resulting formulation would make a useful agricultural pesticide spray, the compounds of formulas (I) and/or (II) encouraging the organic components to remain dispersed in the water, allowing efficient transfer and coverage in treating plants.

Example C

This example illustrates formulations of compounds according to formulas (I) and/or (II) for use as a herbicide emulsion agent. A compound according to formulas (I) and/or (II) or mixture thereof is added to a solvent or solvent mixture and water and a herbicide is incorporated therein and an emulsion formed. The amount of the compound of formulas (I) and/or (II) is generally from about 5 wt. % to about 50 wt. %, preferably from about 10 wt. % to about 40 wt. %, most preferably from about 15 wt. % to about 30 wt. %, of the herbicide concentrate composition. In addition, the compound of formulas (I) and/or (II) can be used in a pesticide emulsion agent formulation that does not incorporate the pesticide itself, instead an appropriate amount of pesticide must be added to the pesticide emulsion agent formulation to make a pesticide emulsion concentrate, which is diluted with water by the user and applied in the dilute form. In general, only 10–30 wt. % of the pesticide emulsion agent formulation is used to in the pesticide emulsion concentrate, that is, there is 70–90 wt. % pesticide in the pesticide emulsion concentrate, which is the form it will generally be commercialized. The final customer will then dilute the pesticide emulsion concentrate (pesticide/emulsifier package) into water for actual application of pesticide.

Example D

As noted above, the compounds of formulas (I) and/or (II) may also be used as an asphalt emulsifier as an additive for asphalt, the possible applications in asphalt products are as a cationic rapid set (CRS) emulsion for chip seal, as a cationic medium set (CMS) for mixing grade applications, in a slurry seal or microsurfacing application, in a roofing and driveway sealer, a cationic slow set emulsion, cationic quick set emulsion, tack coat, fog seal, base stabilization, prime coat, slurry seal, microsurfacing, industrial asphalt emulsion, or filled asphalt emulsion. The amount of the compound of formulas (I) and/or (II) in such an application would likely include from about 0.1 wt. % to about 8.0 wt. %, preferably about 0.20 wt. % to about 5.0 wt. %, and most preferably about 0.5 wt. % to about 2.0 wt. %, of the asphalt.

The pH of the emulsifier solution should be less than about 7.0, and may be adjusted with any strong acid to have a pH of between about 1.0 and about 5.0, preferably between about 2.0 to about 4.0, most preferably between about 2.0 and about 3.0.

Example E

This example illustrates formulations of compounds according to formulas (I) and/or (II) for use in corrosion inhibition, for example, for lubricating oil or oil field use. A compound according to formulas (I) and/or (II) or mixture thereof is added to lubricating or other oils as a corrosion inhibitor, alone or in combination with a surfactant and/or coupling agent, which may be incorporated in the formulation or applied separately. When used, an effective amount is applied to the oil or oil mixture that will come in contact with the metal. The term "effective amount" denotes the amount of compound of formulas (I) and/or (II) that would be effective to inhibit corrosion. In general, the amount of the compound of formulas (I) and/or (II) ranges from about 0.001 wt. % to about 5 wt. %, preferably from about 0.01 wt. % to about 1 wt. %, most preferably from about 0.01 wt. % to about 0.5 wt. %, of the oil mixture in which it is used.

Example F

This example illustrates formulations of compounds according to formulas (I) and/or (II) for use in a lubricant and anti-balling agent for silicate muds and other water-based muds, for example, to lubricate drill strings to prevent stuck pipe, bit-balling, or string balling associated with drilling wells. The apparatus for drilling and general lubrication processes in well-known to those of skill in the art, and are disclosed, for example, in U.S. Pat. Nos. 5,586,608; 5,593,954; and 5,639,715, all of these patents being herein incorporated by reference in their entireties. In this lubrication process, a compound according to formulas (I) and/or (II) or mixture thereof is added to lubricating or other oils effective to inhibit stuck pipe, bit balling, or string balling. The polyamine may be used alone or in combination with a surfactant and/or coupling agent, for example, propylene glycols or ethoxylated glycols, which may be incorporated with the compound of formulas (I) and/or (II) in a formulation or applied separately. Of particular use are the oilfield products available from Witco Corporation under the tradename WITBREAK™, such as WITBREAK™ DPG-484. When used, an effective amount of polyamine is applied to the lubricant mixture as used in the drilling operation. The term "effective amount" denotes the amount of polyamine compound that would be effective to inhibit stuck pipe, bit balling, or string balling. In general, the amount of the compound of formulas (I) and/or (II) ranges from about 0.001 wt. % to about 5 wt. %, preferably from about 0.01 wt. % to about 2 wt. %, most preferably from about 0.05 wt. % to about 0.5 wt. %, of the lubricating mixture in which it is used.

What is claimed is:

1. A process for making a tertiary amine ester of the following formula (I):

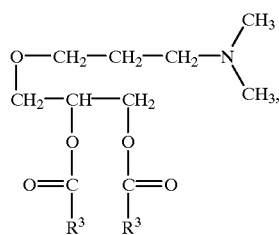

(I)

the process comprising:

(a) reacting a ketone or an aldehyde having the formula

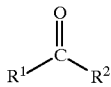

with a glycol to form a ketal or an acetal;

(b) reacting the ketal or the acetal with acrylonitrile to form an ether nitrile;

(c) reducing the ether nitrile to a tertiary amine ketal or a tertiary amine acetal;

(d) hydrolyzing the tertiary amine ketal or the tertiary amine acetal to a tertiary amine diol; and (e) esterifying the tertiary amine diol to the tertiary amine ester of formula (I), wherein $R^1$ and $R^2$ are each independently a hydrogen atom or a linear, branched, or cyclic alkyl, alkylene, alkaryl, or aryl-containing group containing 1 to 18 carbon atoms; and each $R^3$ are each independently of one another fatty acid radicals having 6–22 carbon atoms.

2. The process according to claim 1, further comprising:

(f) protonating or quaternizing the tertiary amine ester of formula (I) to a protonated or quaternary amine ester of the following formula:

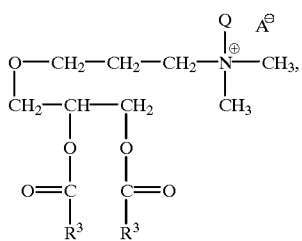

(II)

wherein $A^-$ is an inorganic or organic anion.

3. The process according to claim 2, wherein $A^-$ is selected from the group consisting of: fluoride, chloride, bromide, iodide, chlorite, chlorate, hydroxide, hypophosphite, phosphite, phosphate, carbonate, formate, acetate, lactate, and other carboxylates, oxalate, methyl sulfate, ethyl sulfate, benzoate, and salicylate, and the like.

4. The composition produced by the process of claim 1.

5. The composition according to claim 4, further comprising water.

6. The composition according to claim 5, wherein the amount of compounds of the general formula (I) and/or (II) generally ranges from about 2 wt. % to about 80 wt. % of the total composition.

7. The composition according to claim 6, wherein the amount of compounds of the general formula (I) and/or (II) generally ranges from about 5 wt. % to about 30 wt. % of the total composition.

8. The composition according to claim 4, further comprising at least one conventional quaternary ammonium compound.

9. The composition according to claim 8, wherein the compounds of formula (I) comprise from about 10% to about 90% by weight of the total amount of quaternary ammonium compounds.

10. The composition according to claim 4, further comprising a secondary surfactant selected from the group consisting of: nonionic surfactants, amphoteric surfactants, zwitterionic surfactants, and ionic surfactants.

11. The composition according to claim 10, wherein the secondary surfactant is selected from the group consisting of: ammonium lauryl sulfate, sodium lauryl sulfate, any α-olefin sulfonate, ammonium laureth sulfate (2 or 3 moles), sodium laureth sulfate (2 or 3 moles), sodium myristyl sulfate, sodium myristeth sulfate (1–4 moles), ammonium xylene sulfonate, sodium xylene sulfonate, TEA dodecylbenzene sulfonate, TEA lauryl sulfate, ammonium pareth sulfate, sodium pareth sulfate, sodium oleth sulfate, derivatives thereof, and mixtures thereof.

12. The composition according to claim 10, wherein the secondary surfactant is selected from the group consisting of: betaines, sulfosuccinates, mono- and diglycerides, glycinates, sugars and derivatives thereof, hydroxysultaines, mono- and diacetates, ethoxylated derivatives thereof, and mixtures thereof.

13. The composition according to claim 10, wherein the secondary surfactant is selected from the group consisting of: alkanolamides; amine oxides; nonylphenol ethoxylates; $C_5$–$C_{20}$ linear or branched alcoxylates using EO, PO, BO, or mixtures thereof; amine ethoxylates; fatty amide ethoxylates; fatty acid ethoxylates; carboxylated nonionics; α-polyglucosides; and mixtures thereof.

14. A hydrophilic handle modifier composition comprising:

(a) 15% to 25% by weight of alkyl fatty acid polyglycol ester having 6 to 25 moles of EO;

(b) 45% to 65% by weight of the compounds according to claim 4;

(c) 10% to 20% by weight of partial glyceride esters having 5 to 80 moles of EO; and (d) 5% to 10% by weight of alkyl ether citrates.

15. The hydrophilic handle modifier composition according to claim 14, further comprising:

(e) 0.001% to 10% by weight of silicone compounds.

16. A composition comprising:

(a) at least one compound according to claim 4;

(b) a solvatrope or coupling agent or blends thereof; and (c) an oil or hydrophobic organic component and blends thereof.

17. The composition according to claim 16, wherein the solvatrope or coupling agent is selected from the group consisting of: hydroxypivalyl hydroxypivalate and its alkoxylated derivatives, TMPD, TMPD alkoxylates, ethanol, isopropanol, butanol, 1,2-cyclohexanedimethanol, 1,4-cyclohexanedimethanol, HPHP glycol, isopentyldiol, 1,2-hexanediol, ethylene glycol butyl ether, hexylene glycol, isoprene glycol, sorbitan ethoxylates, 2-butoxyethanol, $C_6$–$C_{12}$ diols/triols and ester diols/triols and their alkoxylated derivatives, glycol ethers, and mixtures thereof.

18. The composition according to claim 16, wherein the oil or hydrophobic organic component is selected from the group consisting of: fatty acids; fatty amides; fatty alcohols; fatty oils; fatty esters made from a $C_8$–$C_{22}$ fatty acid and a $C_1$–$C_8$ alcohol; dialkyl esters; mineral oil; mineral seal oils; silicone oils; petrolatums; monoglycerides; diglycerides; triglycerides; aliphatic, paraffinic, and naphthalinic hydrocarbons; oils and spirits; and mixtures thereof.

19. The composition produced by the process of claim 2.

20. The composition according to claim 19, further comprising water.

21. The composition according to claim 20, wherein the amount of compounds of the general formula (I) and/or (II) generally ranges from about 2 wt. % to about 80 wt. % of the total composition.

22. The composition according to claim 21, wherein the amount of compounds of the general formula (I) and/or (II) generally ranges from about 5 wt. % to about 30 wt. % of the total composition.

23. The composition according to claim 19, further comprising at least one conventional quaternary ammonium compound.

24. The composition according to claim 23, wherein the compounds of formula (I) comprise from about 10% to about 90% by weight of the total amount of quaternary ammonium compounds.

25. The composition according to claim 19, further comprising a secondary surfactant selected from the group consisting of: nonionic surfactants, amphoteric surfactants, zwitterionic surfactants, and ionic surfactants.

26. The composition according to claim 25, wherein the secondary surfactant is selected from the group consisting of: ammonium lauryl sulfate, sodium lauryl sulfate, any α-olefin sulfonate, ammonium laureth sulfate (2 or 3 moles), sodium laureth sulfate (2 or 3 moles), sodium myristyl sulfate, sodium myristeth sulfate (1–4 moles), ammonium xylene sulfonate, sodium xylene sulfonate, TEA dodecylbenzene sulfonate, TEA lauryl sulfate, ammonium pareth sulfate, sodium pareth sulfate, sodium oleth sulfate, derivatives thereof, and mixtures thereof.

27. The composition according to claim 25, wherein the secondary surfactant is selected from the group consisting of: betaines, sulfosuccinates, mono- and diglycerides, glycinates, sugars and derivatives thereof, hydroxysultaines, mono- and diacetates, ethoxylated derivatives thereof, and mixtures thereof.

28. The composition according to claim 25, wherein the secondary surfactant is selected from the group consisting of: alkanolamides; amine oxides; nonylphenol ethoxylates; $C_5$–$C_{20}$ linear or branched alcoxylates using EO, PO, BO, or mixtures thereof; amine ethoxylates; fatty amide ethoxylates; fatty acid ethoxylates; carboxylated nonionics; α-polyglucosides; and mixtures thereof.

29. A hydrophilic handle modifier composition comprising:

(a) 15% to 25% by weight of alkyl fatty acid polyglycol ester having 6 to 25 moles of EO;

(b) 45% to 65% by weight of the compounds according to claim 19;

(c) 10% to 20% by weight of partial glyceride esters having 5 to 80 moles of EO; and (d) 5% to 10% by weight of alkyl ether citrates.

30. The hydrophilic handle modifier composition according to claim 29, further comprising:

(e) 0.001% to 10% by weight of silicone compounds.

31. A composition comprising:

(a) at least one compound according to claim 19;

(b) a solvatrope or coupling agent or blends thereof; and (c) an oil or hydrophobic organic component and blends thereof.

32. The composition according to claim 31, wherein the solvatrope or coupling agent is selected from the group consisting of: hydroxypivalyl hydroxypivalate and its alkoxylated derivatives, TMPD, TMPD alkoxylates, ethanol, isopropanol, butanol, 1,2-cyclohexanedimethanol, 1,4-cyclohexanedimethanol, HPHP glycol, isopentyidiol, 1,2-hexanediol, ethylene glycol butyl ether, hexylene glycol, isoprene glycol, sorbitan ethoxylates, 2-butoxyethanol, $C_6$–$C_{12}$ diols/triols and ester diols/triols and their alkoxylated derivatives, glycol ethers, and mixtures thereof.

33. The composition according to claim 31, wherein the oil or hydrophobic organic component is selected from the group consisting of: fatty acids; fatty amides; fatty alcohols; fatty oils; fatty esters made from a $C_8$–$C_{22}$ fatty acid and a $C_1$–$C_8$ alcohol; dialkyl esters; mineral oil; mineral seal oils; silicone oils; petrolatums; monoglycerides; diglycerides; triglycerides; aliphatic, paraffinic, and naphthalinic hydrocarbons; oils and spirits; and mixtures thereof.

* * * * *